US010478437B2

(12) United States Patent
Qian et al.

(10) Patent No.: US 10,478,437 B2
(45) Date of Patent: Nov. 19, 2019

(54) COMBINATION THERAPY TO ENHANCE THE ANTICANCER EFFICACY OF PLATINUM DRUGS

(71) Applicant: University of Pittsburgh-of the Commonwealth System of Higher Education, Pittsburgh, PA (US)

(72) Inventors: Wei Qian, Pittsburgh, PA (US); Peter Wipf, Pittsburgh, PA (US); Bennett Van Houten, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/380,776

(22) Filed: Dec. 15, 2016

(65) Prior Publication Data
US 2017/0095478 A1    Apr. 6, 2017

Related U.S. Application Data

(63) Continuation of application No. PCT/US2015/036485, filed on Jun. 18, 2015.

(60) Provisional application No. 62/013,943, filed on Jun. 18, 2014.

(51) Int. Cl.
| | |
|---|---|
| *A61K 31/517* | (2006.01) |
| *A61K 31/513* | (2006.01) |
| *A61K 31/428* | (2006.01) |
| *A61K 31/44* | (2006.01) |
| *A61K 31/282* | (2006.01) |
| *A61K 31/4436* | (2006.01) |
| *A61K 33/24* | (2019.01) |
| *A61K 45/06* | (2006.01) |

(52) U.S. Cl.
CPC .......... *A61K 31/517* (2013.01); *A61K 31/282* (2013.01); *A61K 31/428* (2013.01); *A61K 31/44* (2013.01); *A61K 31/4436* (2013.01); *A61K 31/513* (2013.01); *A61K 33/24* (2013.01); *A61K 45/06* (2013.01)

(58) Field of Classification Search
CPC .................................................. A61K 31/517
See application file for complete search history.

(56) References Cited

U.S. PATENT DOCUMENTS

| 8,450,333 | B2 * | 5/2013 | Nunnari | C07D 239/95 |
| | | | | 514/266.31 |
| 2003/0229108 | A1 * | 12/2003 | De Belin | A61K 31/515 |
| | | | | 514/269 |
| 2005/0038051 | A1 | 2/2005 | Nunnari et al. | |
| 2008/0287473 | A1 | 11/2008 | Nunnari et al. | |
| 2012/0294956 | A1 | 11/2012 | Qian et al. | |

OTHER PUBLICATIONS

Ghorab et al., Phosphorous, Sulfur, and Silicon (2008), 183(12), pp. 2906-2917.*
Abdel Gawad et al., "Synthesis and antitumor activity of some 2, 3-disubstituted quinazolin-4(3H)-ones and 4, 6-disubstituted-1, 2, 3, 4-tetrahydroquinazolin-2H-ones," European Journal of Medicinal Chemistry 45:6058-6067 (2010).
Al-Omary et al., "Non-classical antifolates. Part 2: Synthesis, biological evaluation, and molecular modeling study of some new 2,6-substituted-quinazolin-4-ones," Bioorganic & Medicinal Chemistry 18:2849-2863 (2010).
International Search Report dated Sep. 1, 2015 in International Application No. PCT/US2015/036485.
Andrews et al., "Cellular Pharmacology of Cisplatin: Perspectives on Mechanisms of Acquired Resistance," Cancer Cells 2(2):35-43 (1990).
Chou, "Drug Combination Studies and Their Synergy Quantification Using the Chou-Talalay Method," Cancer Res. 70:440-446 (2010).
Chou, "Theoretical Basis, Experimental Design, and Computerized Simulation of Synergism and Antagonism in Drug Combination Studies," Pharmacol Rev. 58:621-681 (2006).
Galluzzi et al., "Molecular mechanisms of cisplatin resistance," Oncogene 31:1869-1883 (2012).
Mullany et al., "Minireview: Animal Models and Mechanisms of Ovarian Cancer Development," Endocrinology 153(4):1585-1592 (2012).
Qian et al., "Mitochondrial hyperfusion induced by loss of the fission protein Drp1 causes ATM-dependent G2/M arrest and aneuploidy through DNA replication stress," J Cell Sci. 125(23):5745-5757 (2012).
Qian et al., "Novel combination of mitochondrial division inhibitor 1 (mdivi-1) and platinum agents produces synergistic pro-apoptotic effect in drug resistant tumor cells," Oncotarget 5(12):4180-4194 (2014) with Suppl. Information.
Qian et al., "Alterations in bioenergetics due to changes in mitochondrial DNA copy number," Methods 51:452-457 (2010).
Romero et al., "Minireview: Human Ovarian Cancer: Biology, Current Management, and Paths to Personalizing Therapy," Endocrinology 153(4):1593-1602 (2012).
Runowicz, "Advances in the Screening and Treatment of Ovarian Cancer," CA: a cancer Journal for Clinicians 42(6):327-349 (1992).
Stewart et al., "Proteins Associated with Cisplatin Resistance in Ovarian Cancer Cells Identified by Quantitative Proteomic Technology and Integrated with mRNA Expression Levels," Mol. & Cell Proteomics 5:433-443 (2006).
Wang et al., "Predominant requirement of Bax for apoptosis in HCT116 cells is determined by Mcl-1's inhibitory effect on Bak," Oncogene 31:3177-3189 (2012).
Wang et al., "Cellular Processing of Platinum Anticancer Drugs," Nature Reviews. Drug Discovery 4:307-320 (2005).

* cited by examiner

*Primary Examiner* — Brian J Davis
(74) *Attorney, Agent, or Firm* — Baker Botts L.L.P.

(57) ABSTRACT

The present invention relates to compositions and methods for reducing cell proliferation and/or promoting cell death. It is based, at least in part, on the discovery that in platinum drug-resistant cell lines, certain compounds, together with a second antiproliferative agent (e.g., cisplatin), act synergistically to promote apoptosis. Accordingly, the present invention provides for novel anticancer strategies.

35 Claims, 15 Drawing Sheets

COMBINATION THERAPY TO ENHANCE THE ANTICANCER EFFICACY OF PLATINUM DRUGS

CROSS-REFERENCE TO RELATED APPLICATIONS

Figure 1:
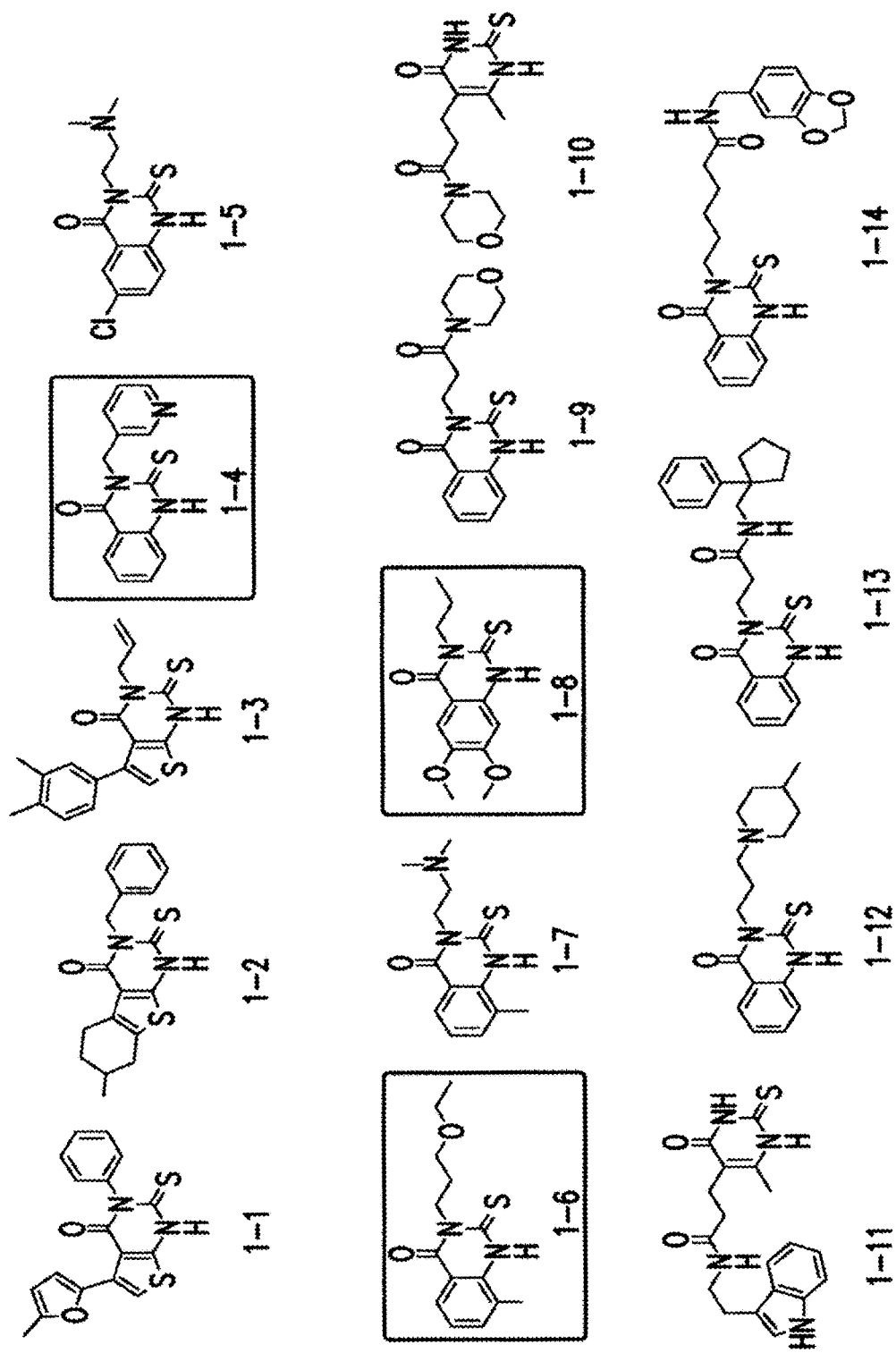
Figure 1:
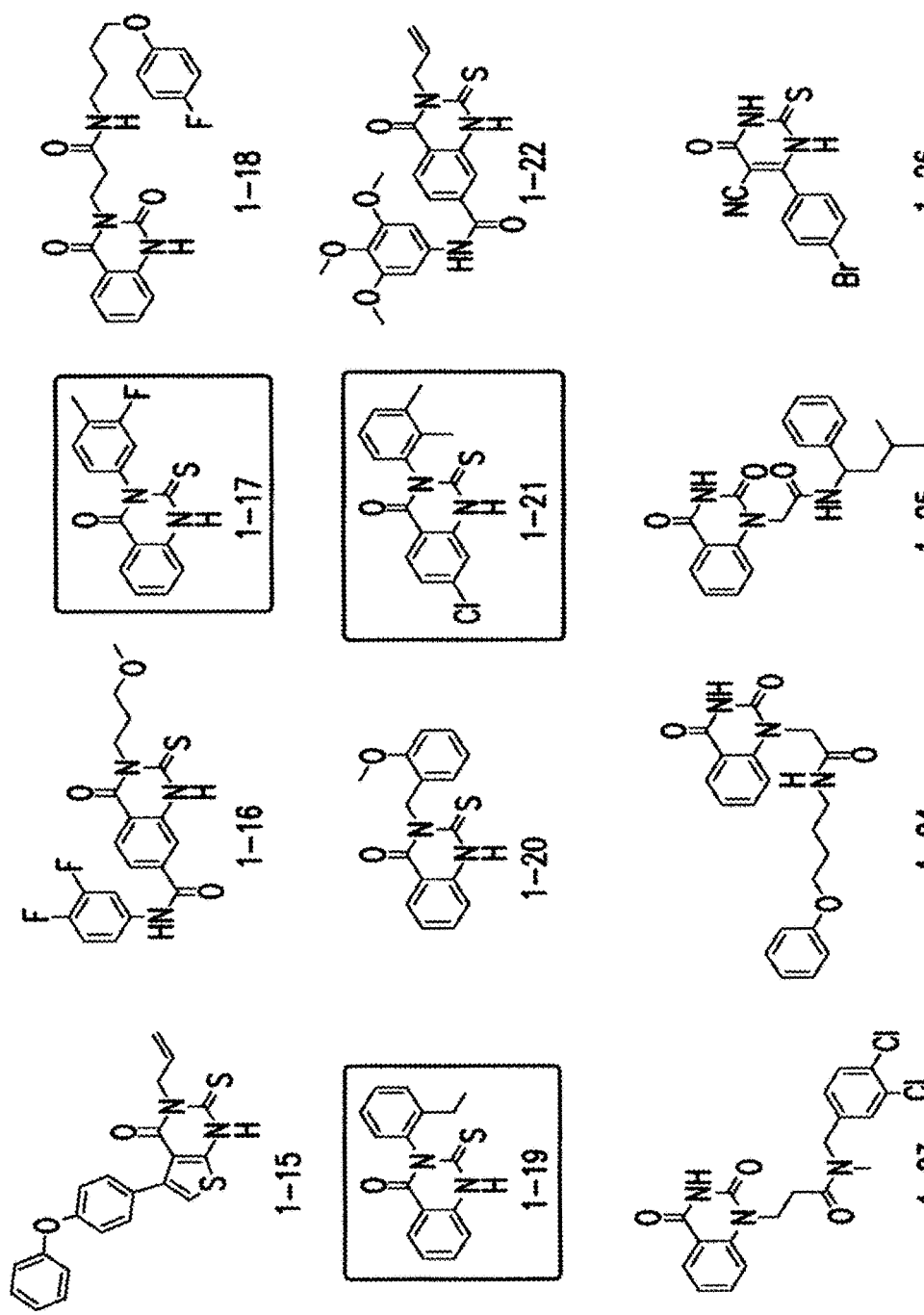
Figure 1:
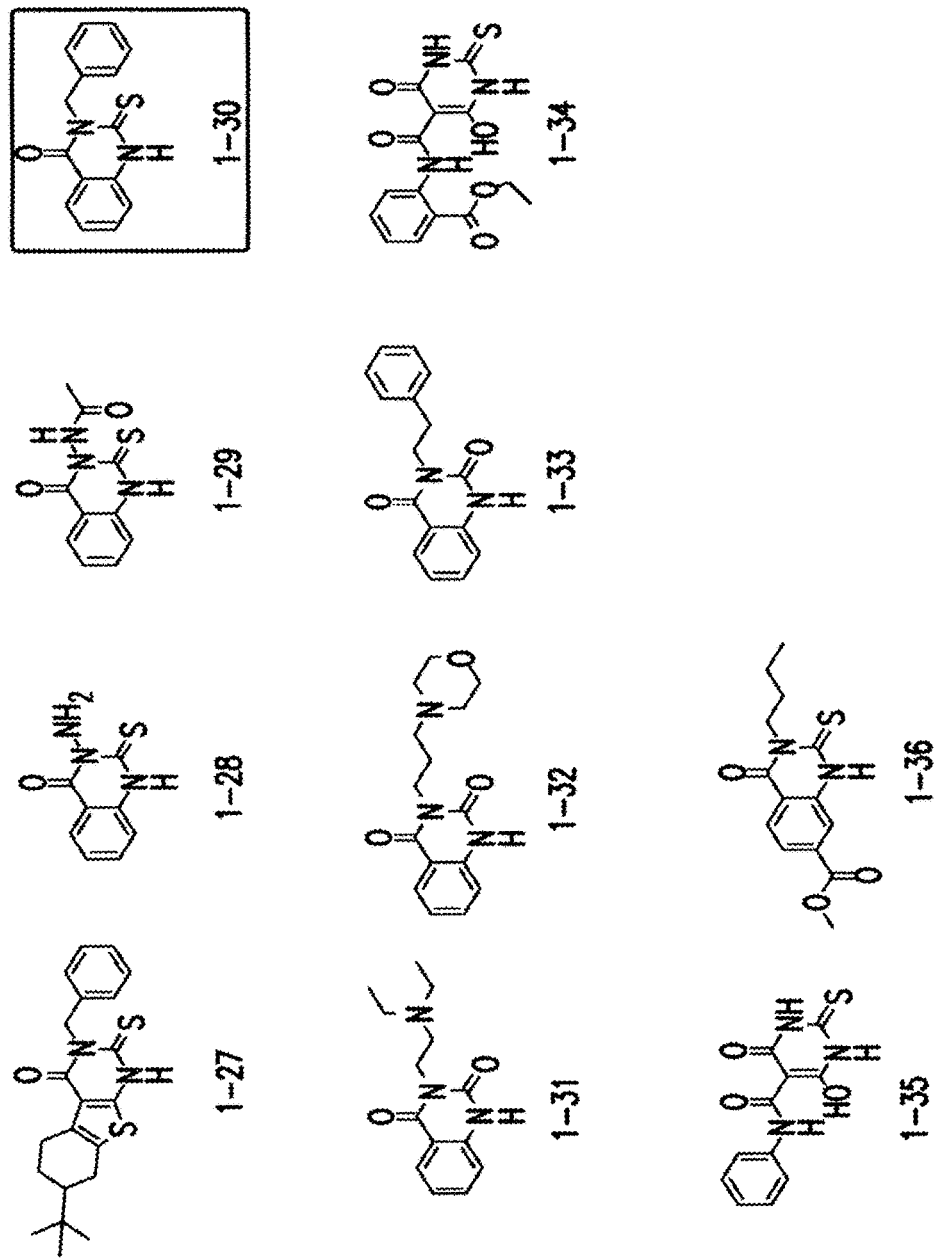

This application is a continuation of International Patent Application Serial No. PCT/US2015/036485, filed Jun. 18, 2015, and claims priority to U.S. Provisional Application Ser. No. 62/013,943, filed Jun. 18, 2014, to both of which priority is claimed and the contents of both of which are incorporated herein in their entireties.

1. INTRODUCTION

The present invention relates to methods and compounds to be used for reducing cell proliferation and/or promoting cell death. It further relates to methods of treating cancer which employ the compounds in combination with a platinum-based anticancer drug.

2. BACKGROUND OF THE INVENTION

The platinum-based anticancer drugs, including cisplatin and carboplatin, are among the most potent and widely used chemotherapeutic agents. They alone or in combination with other drugs are the standard of care for treating a variety of cancers, including testicular, ovarian, colorectal, bladder, lung, and head and neck cancers (Wang and Lippard, 2005). The major limitations for the clinical application of these platinum drugs are their inherent toxicities, as well as the high incidence of intrinsic and acquired drug resistance by tumors (Andrews and Howell, 1990; Galluzzi et al., 2012). Development of platinum drug resistance is also often associated with multidrug resistant phenotype in tumor cells. In particular for ovarian cancer, which is the leading cause of death from gynecologic malignancies, platinum drugs are used as standard first-line therapy (Mullany and Richards, 2012), with the initial response rate of up to 70% (Runowicz, 1992). However, 70% of those patients experience disease recurrence (Romero and Bast, 2012).

Resistance to platinum therapy, which is associated with incurable disease, eventually occurs in all patients treated for recurrent ovarian cancer, in addition to the approximately one-third of all women who are intrinsically resistant to cisplatin during primary treatment (Stewart et al., 2006). Platinum resistance is one of the most important factors in determining prognosis of ovarian cancer. Despite the extensive efforts that have been made to understand the complex mechanism underlying cellular resistance to platinum-based anticancer drugs, the nature of platinum drug resistance has not been clearly established (Wang and Lippard, 2005). To date, overcoming platinum drug resistance by pharmacological manipulation still represents a major clinical challenge. Therefore, there is a need in the art for strategies that can overcome cisplatin resistance and improve clinical outcomes.

3. SUMMARY OF THE INVENTION

The present invention relates to compositions and methods for reducing cell proliferation and/or promoting cell death. It is based, at least in part, on the discovery that in platinum drug-resistant cell lines, certain compounds, together with a second antiproliferative agent (e.g., cisplatin), act synergistically to promote apoptosis. Accordingly, the present invention provides for novel anticancer strategies.

4. BRIEF DESCRIPTION OF THE FIGURES

FIG. 1. Structures of compounds according to certain non-limiting embodiments of the present invention.

Figure 2:
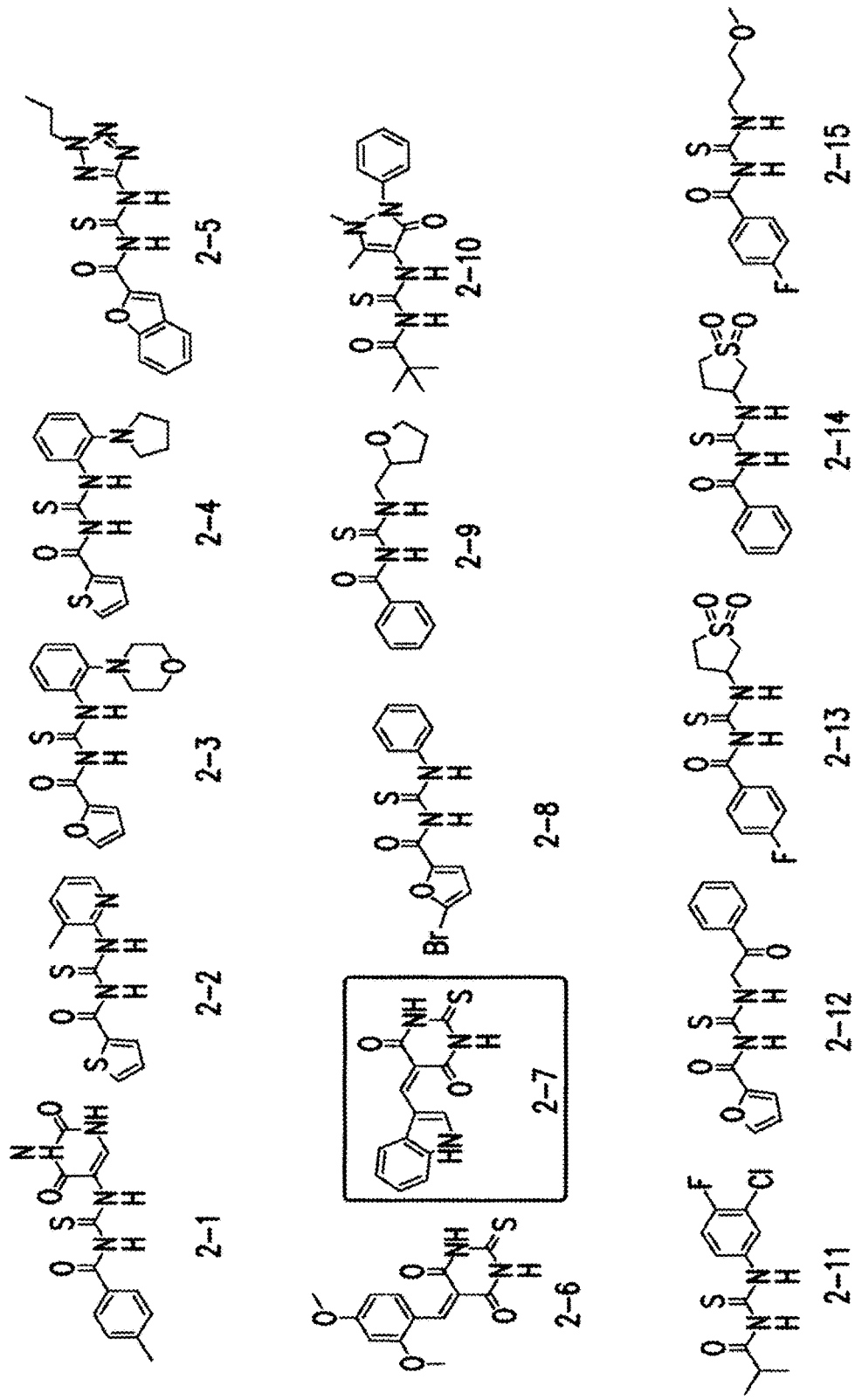
Figure 2:
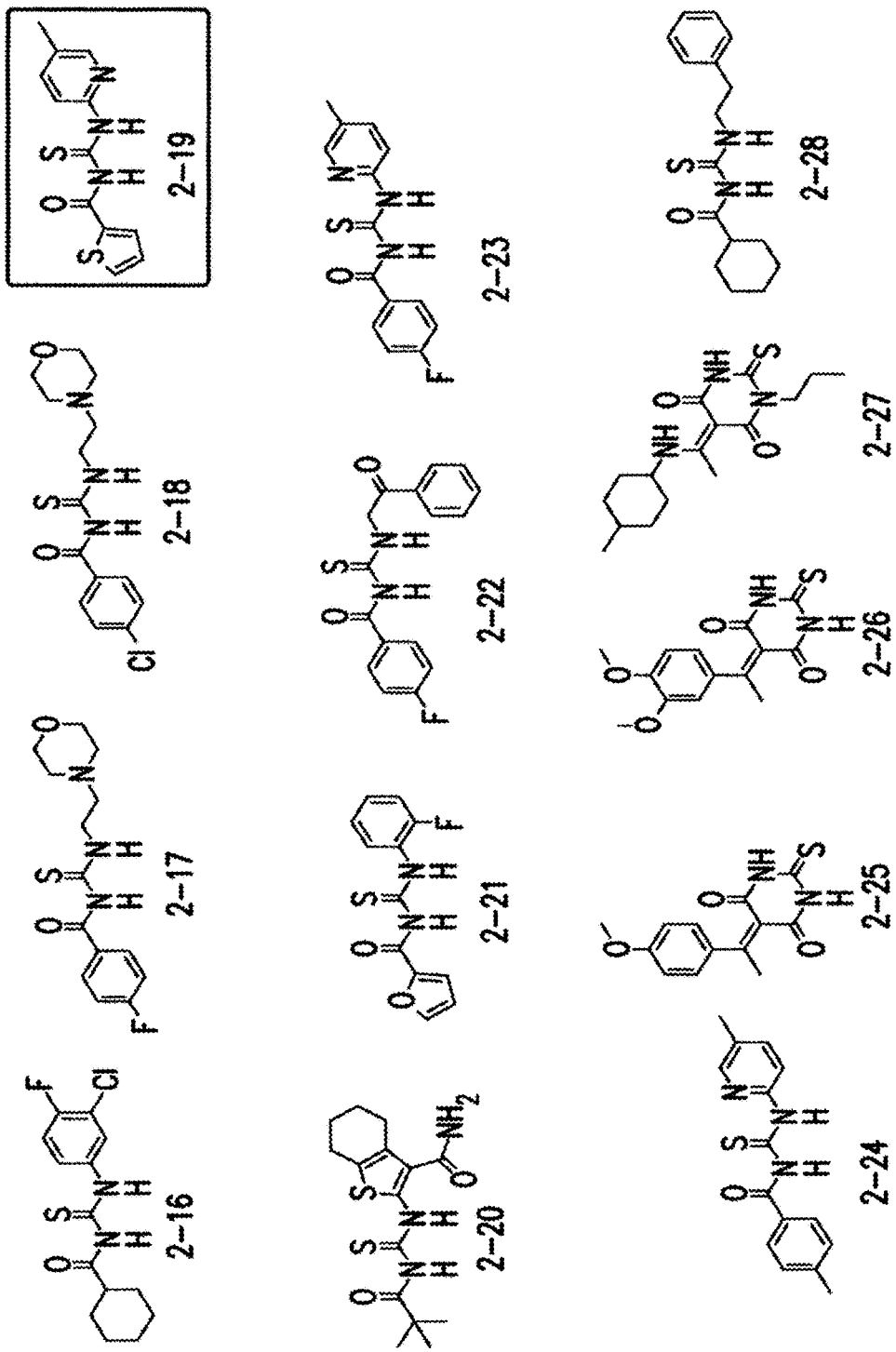
Figure 2:
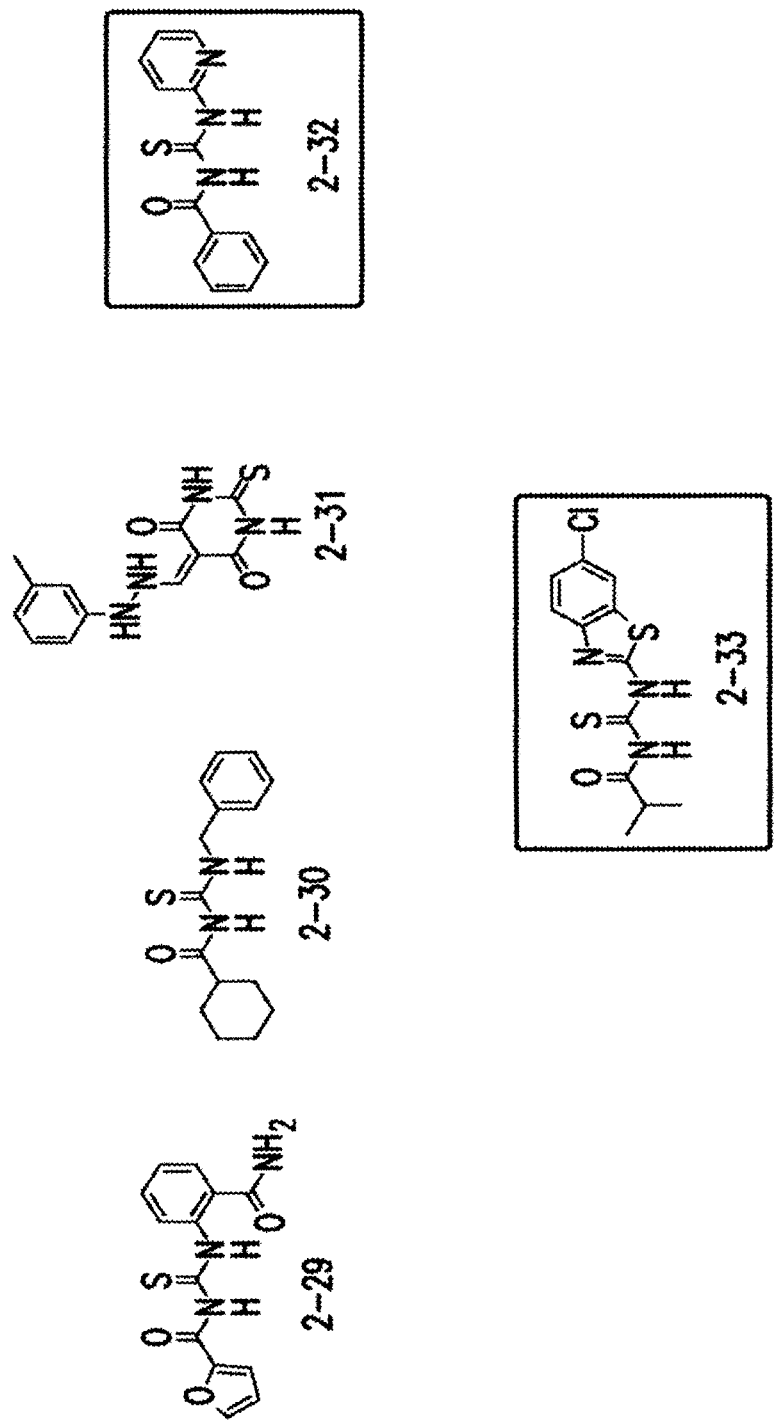

FIG. 2. Structures of compounds according to certain non-limiting embodiments of the present invention.

Figure 3:
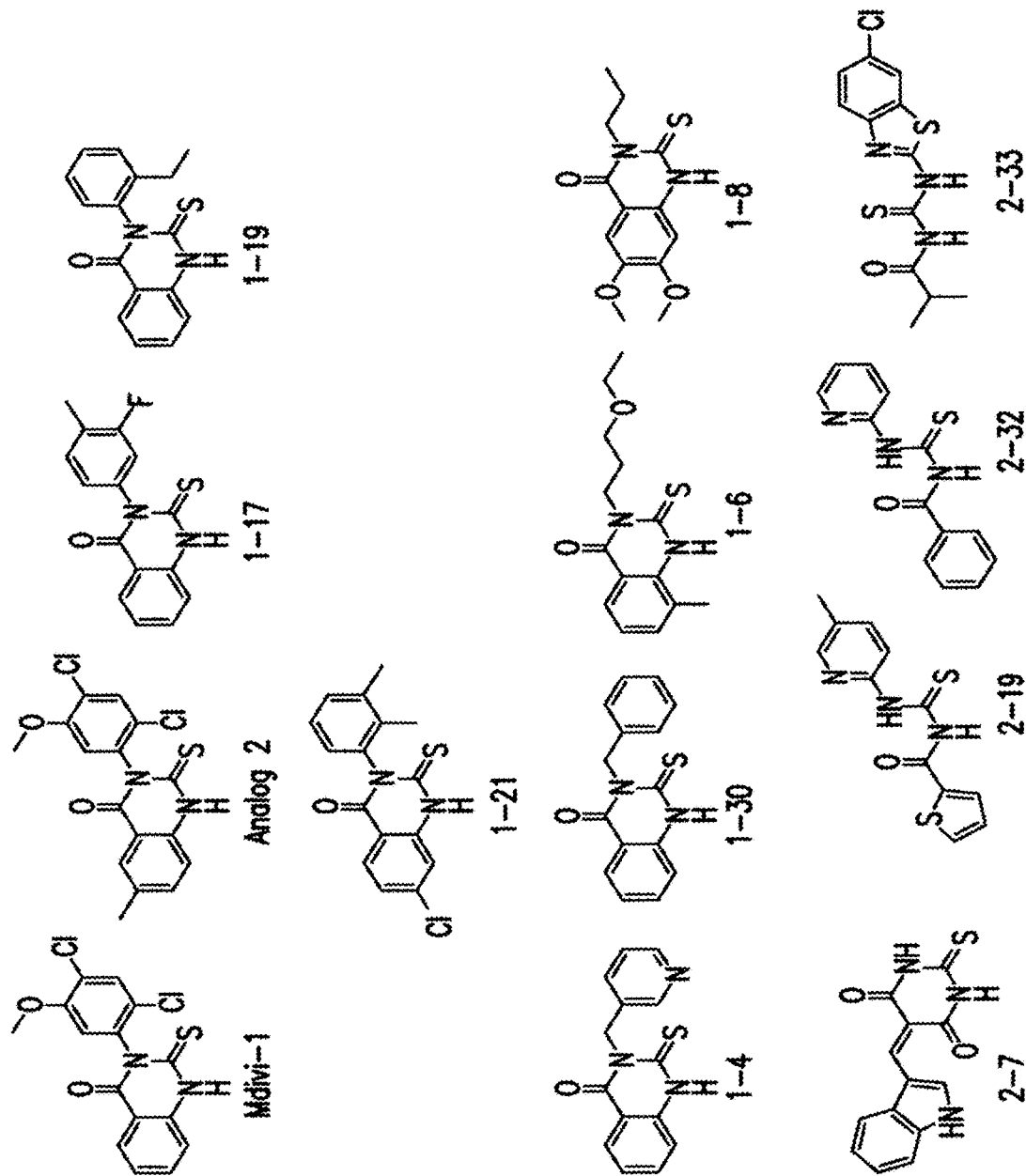

FIG. 3. Structures of compounds according to certain non-limiting embodiments of the present invention.

Figure 4:
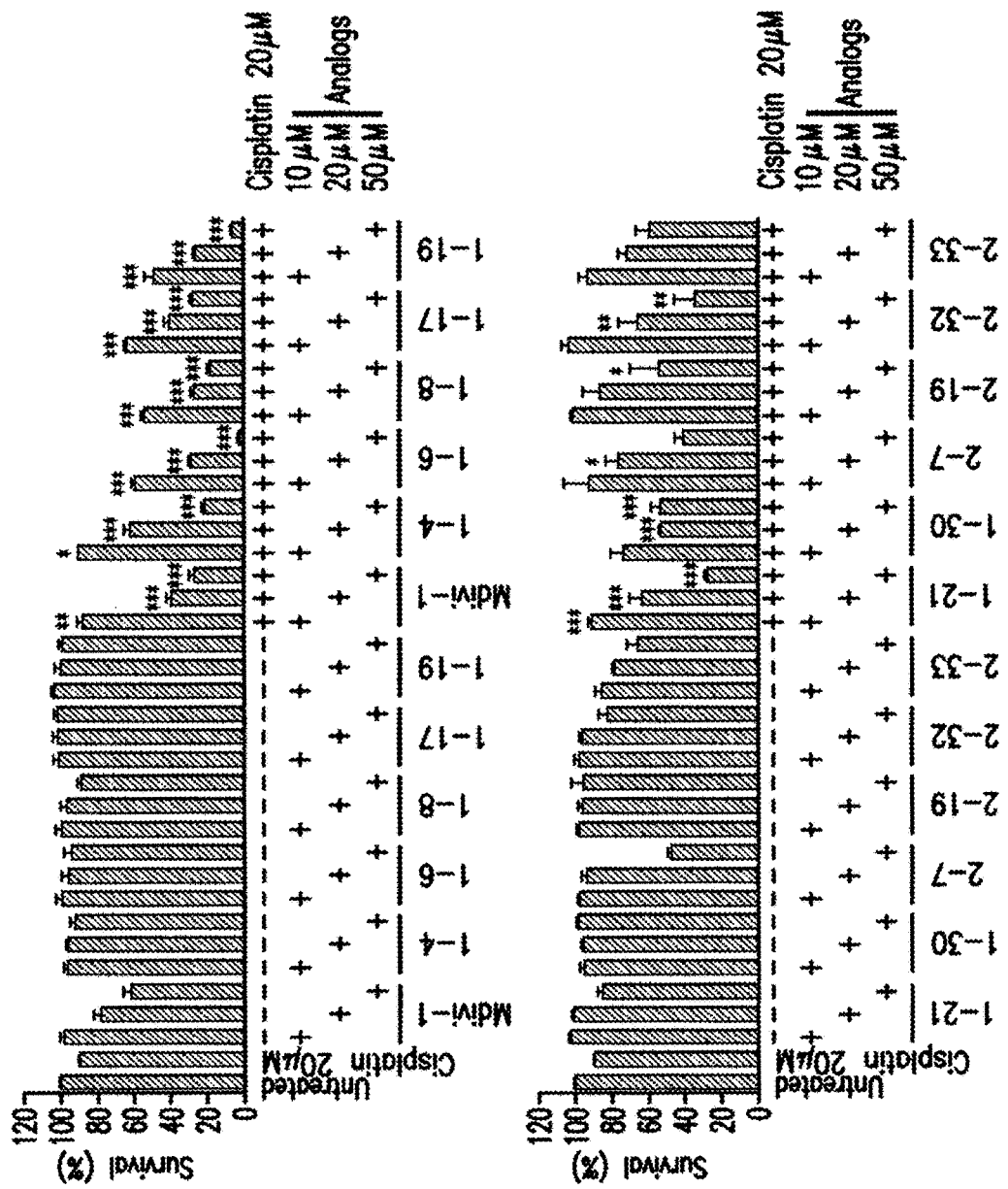

FIG. 4. Synergistic cytotoxicity of various concentrations of active compounds in combination with cisplatin in cisplatin-resistant ovarian cancer cells. A2780cis cells were treated with cisplatin alone, compounds alone or combination at indicated concentrations for 24 h. Cell viability was determined by CellTiter-Blue assay. Data represent the mean±SD of triplicates. *P<0.05,P<0.01, *P<0.001.

Figure 5:
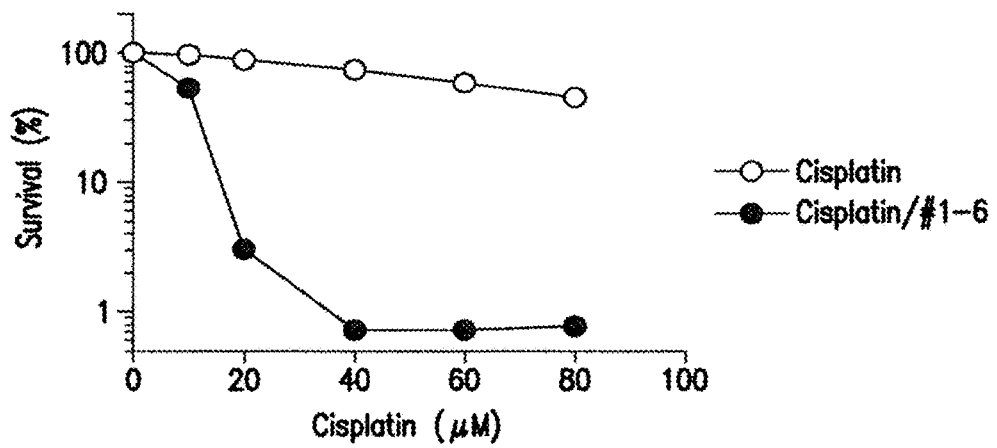

FIG. 5. Short-term exposure of A2780cis cells to the combination of cisplatin and compound 1-6 dramatically reduces cell survival. A2780cis cells were treated with increasing doses of cisplatin alone or the combination of cisplatin with compound 1-6 (20 µM) for 3 h. The compounds were then washed out. Cell survival was determined after 48 h incubation of cells in compound free media by CellTiter-Blue assay.

Figure 6:
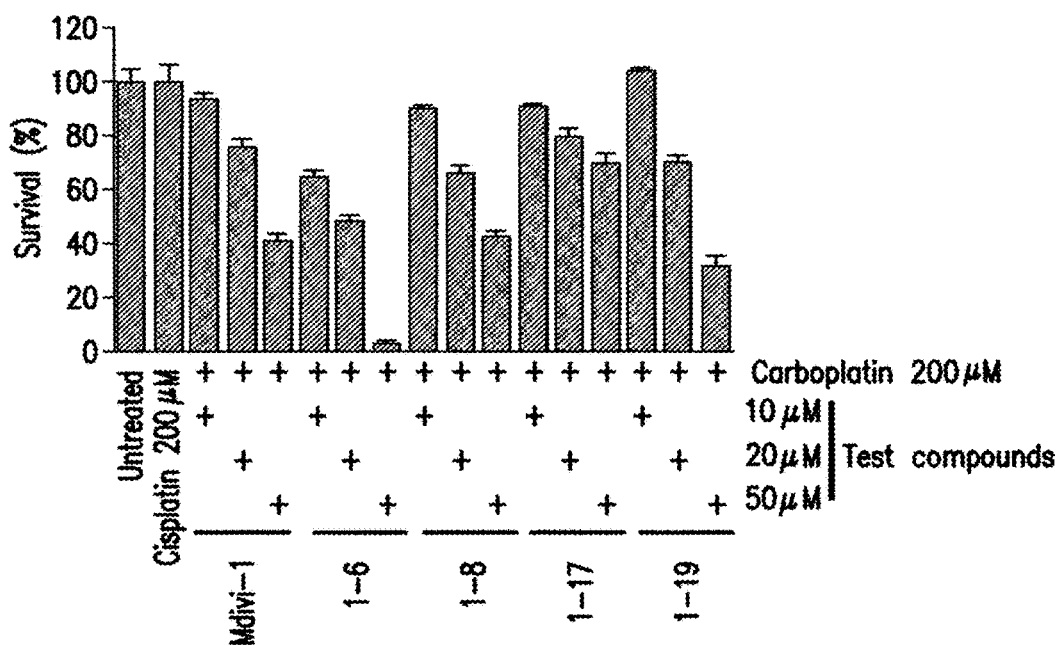

FIG. 6. The disclosed compounds enhance the efficacy of carboplatin. A2780cis cells were treated with carboplatin alone or with the combination of carboplatin and compounds at indicated concentrations for 24 h. Cell viability was determined by CellTiter-Blue.

Figure 7A:
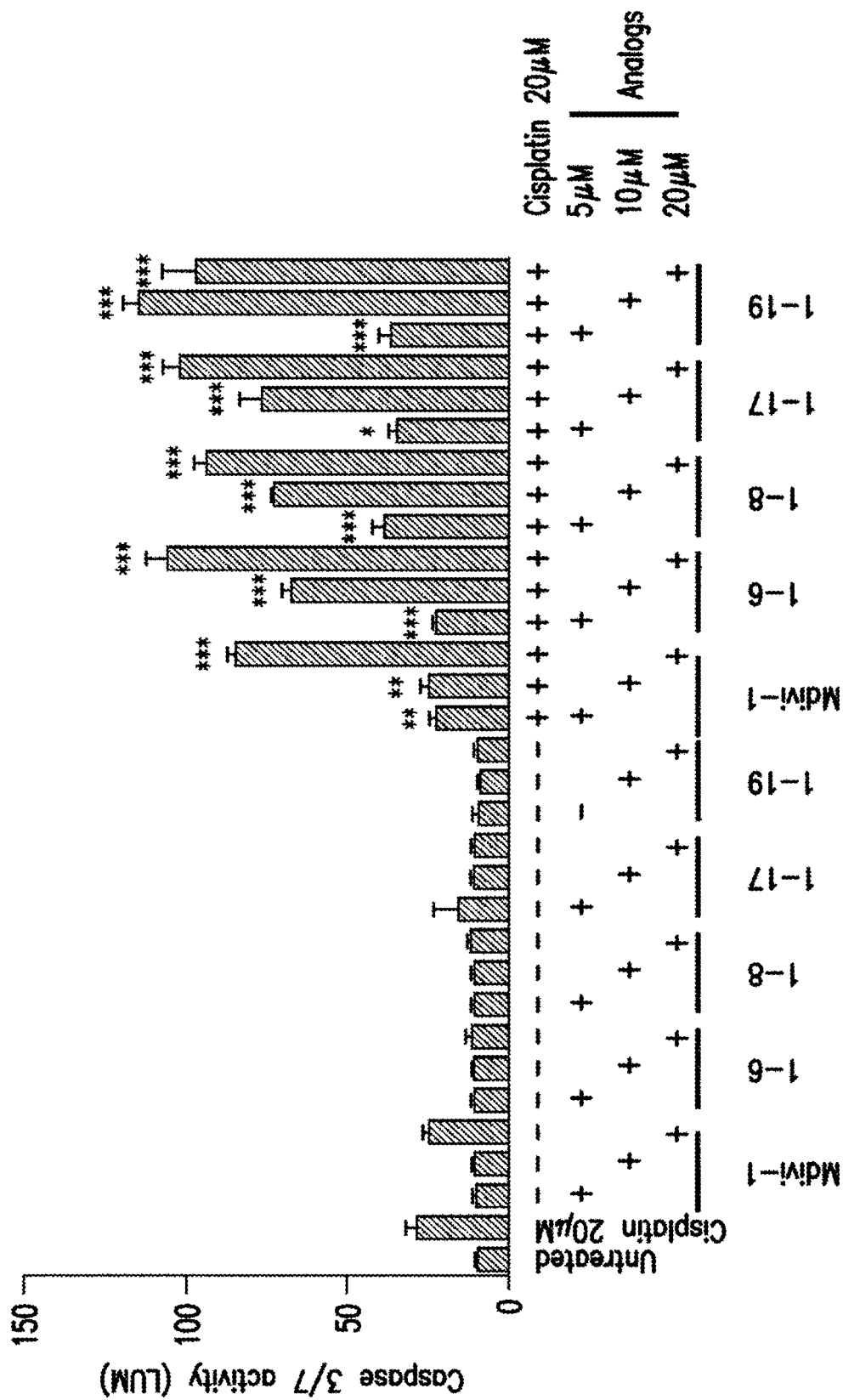
Figure 7B:
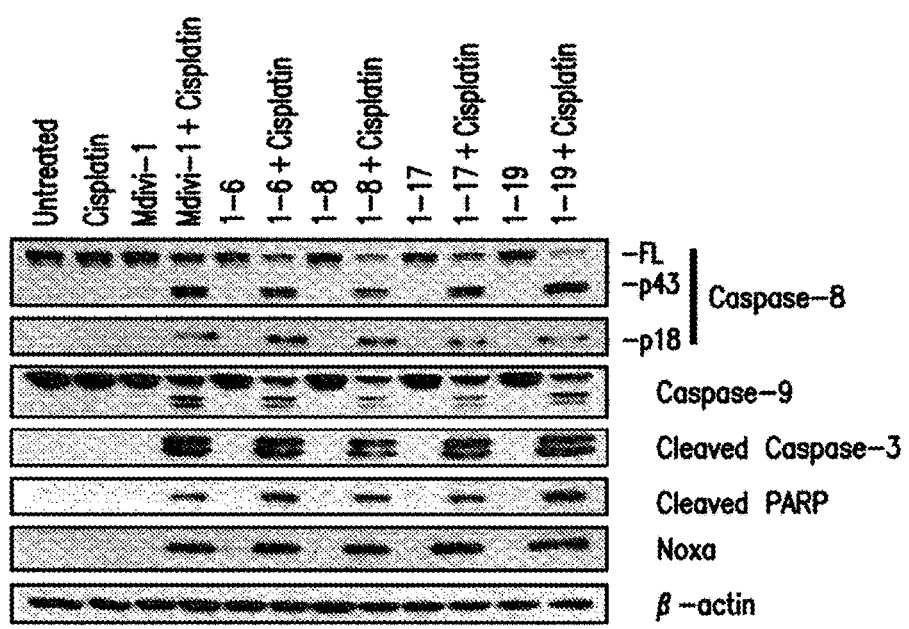

FIG. 7A-B. The combination of cisplatin and the disclosed compounds induces apoptotic cell death. (A) A2780cis cells were treated with cisplatin alone, compounds alone or combination at indicated concentrations for 20 h. Apoptotic cell death was determined by the activation of caspase-3/7. Data represent the mean±SD of triplicates. * P<0.05, P<0.01, *P<0.001. (B) A2780cis cells were treated with cisplatin (20 µM) alone, compounds (20 µM) alone or the combination for 20 h. The cleavage of Caspase-8, 9, 3, PARP and the induction of Noxa was examined by western blot. The human specific anti-caspase-8 antibody recognizes both the full length (FL) and the cleaved fragments.

Figure 8A:
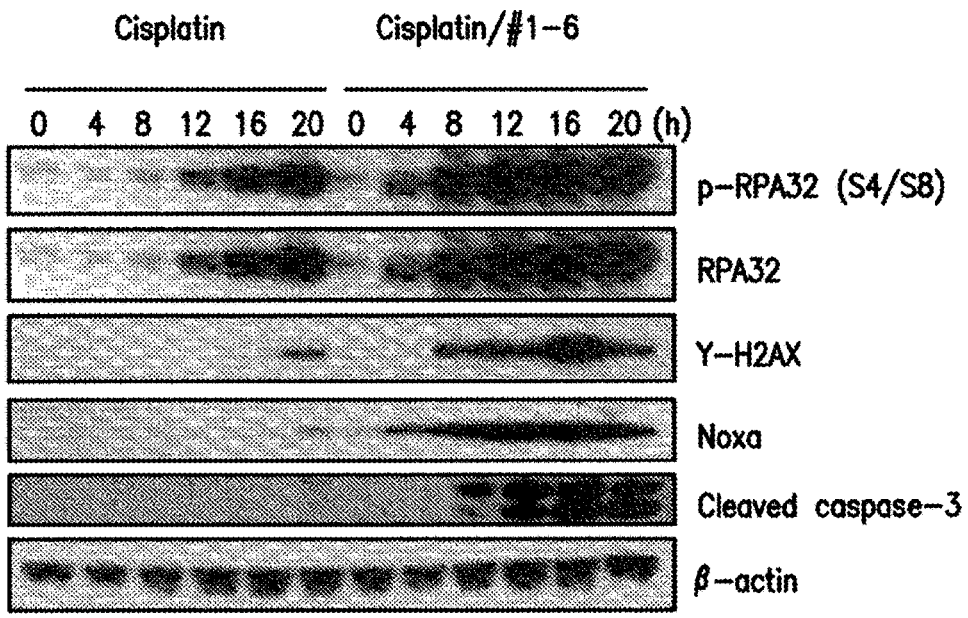
Figure 8B:
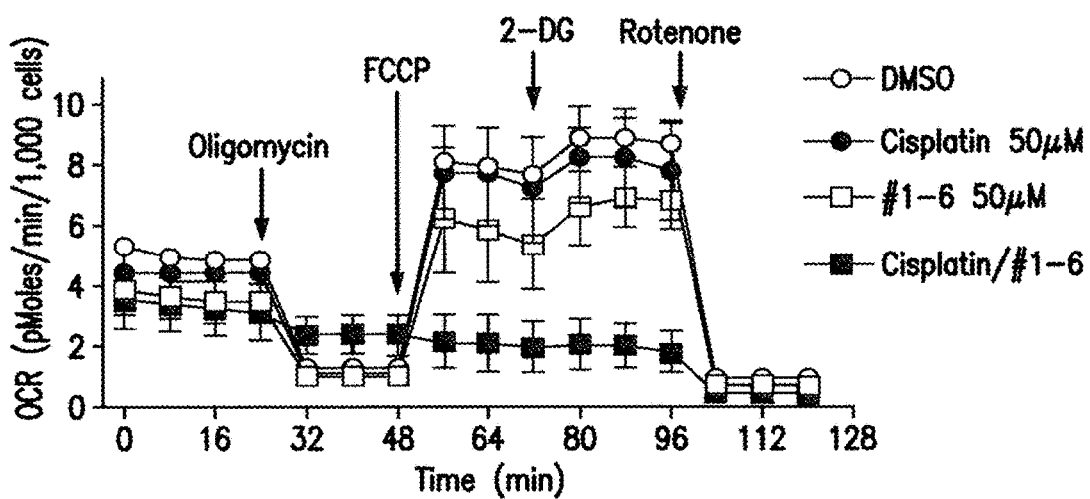
Figure 8C:
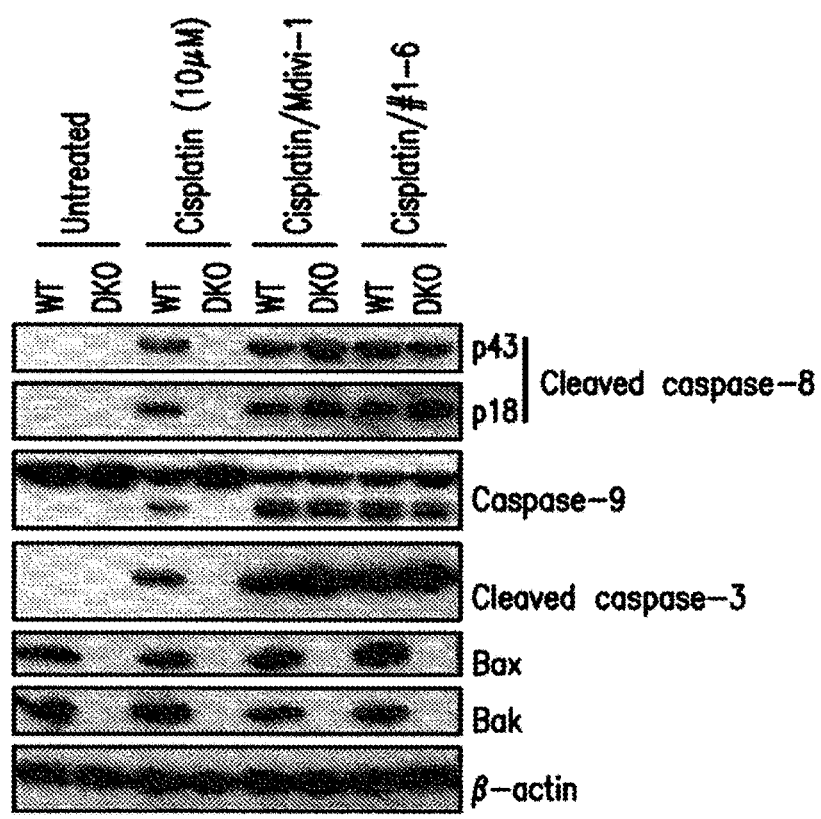

FIG. 8A-C. The combination of cisplatin and the disclosed compounds enhances DNA damage and mitochondrial dysfunction leading to hyperactivation of intrinsic mitochondrial apoptotic signaling independent of Bax and Bak. (A) A2780cis cells were treated with cisplatin (20 µM) alone or the combination of cisplatin with compound 1-6 (20 µM) for the indicated time points. The phosphorylation of RPA32 and histone H2AX, the induction of Noxa, and cleavage of Caspase-3 were determined by western blot. (B) A2780cis cells were treated with cisplatin (50 µM) alone, compound 1-6 (50 µM) alone or the combination for 4 h. The OCR was measured by a Seahorse XF24 extracellular flux analyzer. Data represent the mean±SD of triplicates. (C) Bax/Bak wildtype (WT) and double knockout (DKO) MEF cells were treated with cisplatin (10 µM) alone, or the combination with mdivi-1 (20 µM) or compound 1-6 (20 µM) for 20 h. The cleavage of Caspase-8, 9, and 3 were determined by western blot. The mouse specific anti-Caspase-8 antibody recognizes only the cleaved fragments as compared to human specific antibody.

Figure 9:
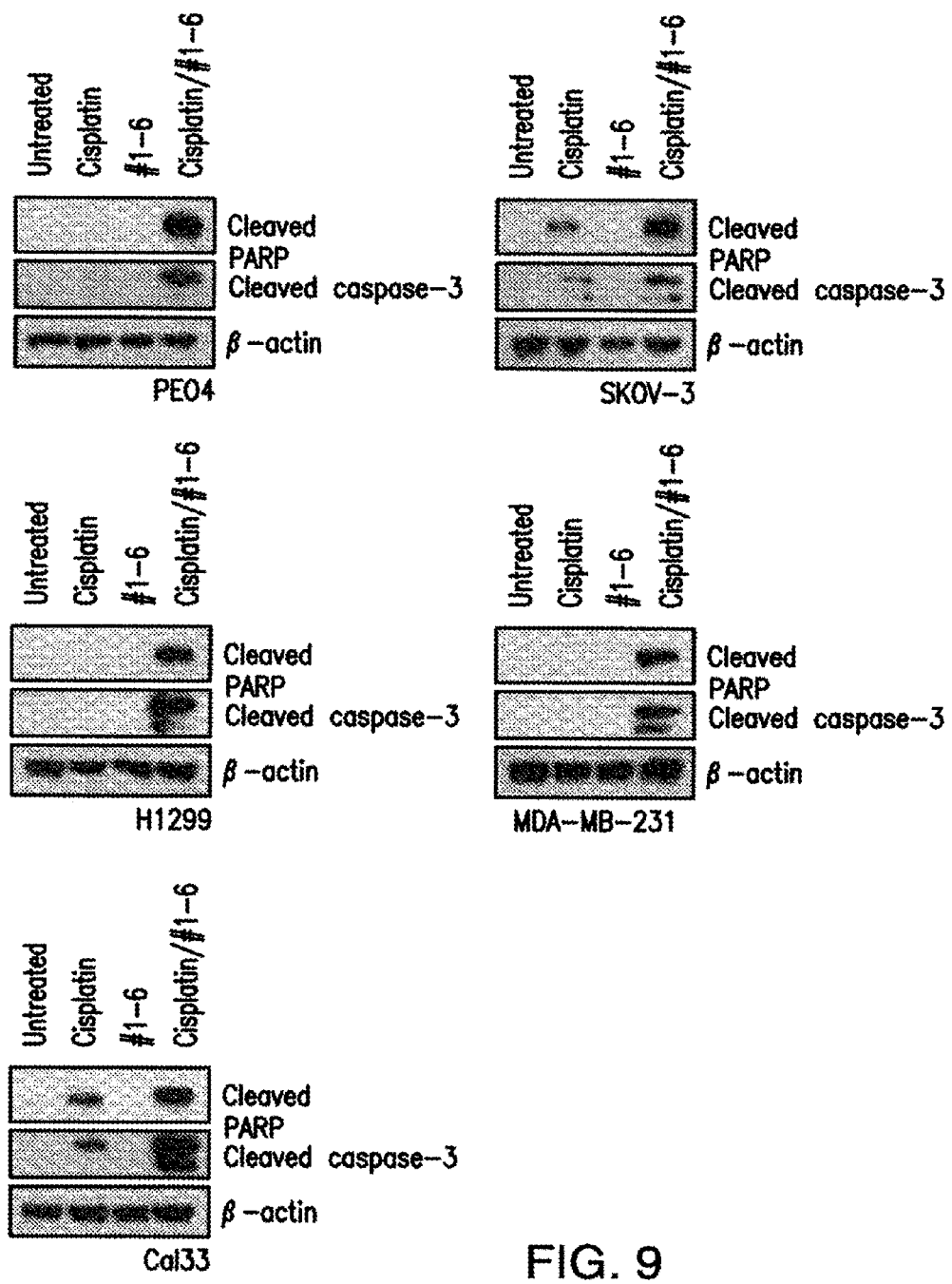

FIG. 9. The combination of cisplatin and compound 1-6 triggers extensive apoptosis in various types of cisplatinand multidrug-resistant tumor cells. Cisplatin-resistant cancer cells PEO4 (ovarian), SKOV3 (ovarian), H1299 (lung), MDA-MB-231 (breast), Ca133 (head & neck) were treated with DMSO (untreated), cisplatin (20 μM) alone, compound 1-6 (20 μM) alone, or the combination for 20 h. Cleavage of PARP and Caspase-3 were determined by western blot.

Figure 10:
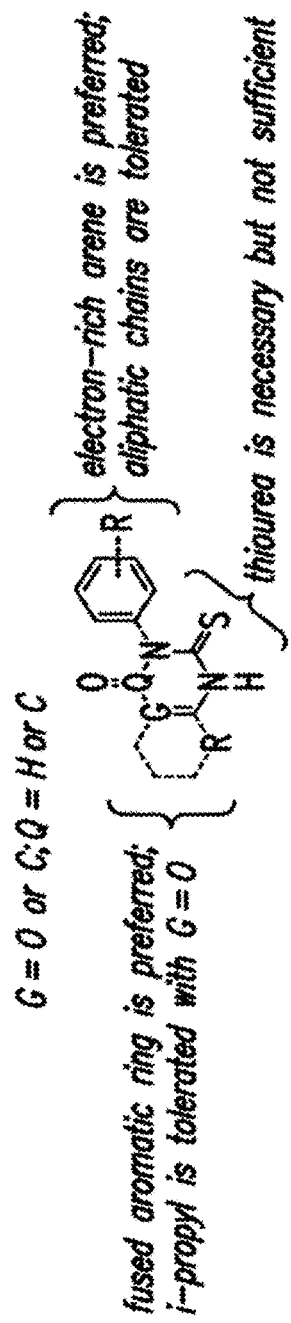

FIG. 10. Pharmacophore model. G=O or C; Q=H or C.

5. DETAILED DESCRIPTION OF THE INVENTION

For clarity and not by way of limitation, the detailed description is divided into the following subsections:
(i) compounds;
(ii) formulations;
(iii) agents for use with the disclosed compounds;
(iv) methods of treatment; and
(v) kits.

5.1 Compounds

In certain non-limiting embodiments, compounds that may be used according to the invention include small molecule compounds such as the compounds depicted in FIGS. 1 and 2, or salt forms thereof. FIG. 3 displays the compounds boxed in FIGS. 1 and 2.

In certain non-limiting embodiments, the present invention relates to a compound of Formula I:

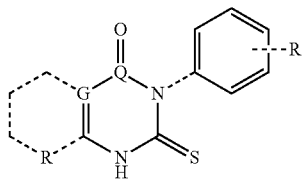

wherein G can be selected from O or C; Q can be selected from H or C; and R can be selected from H, N, a substituted or unsubstituted alkyl, a fluorinated or partially fluorinated alkyl, a sulfur, a halogen, cyano, azido, hydroxyl, a substituted or unsubstituted sulfonyl.

In certain non-limiting embodiments, the present invention relates to a compound of Formula II (corresponding to compound 1-21 of Example 1):

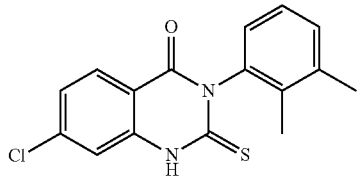 [SMILES: Cc1cccc(-n2c(=S)[nH]c3cc(Cl)ccc3c2=O)c1C]

In certain non-limiting embodiments, the present invention relates to a compound of Formula III (corresponding to compound 1-17 of Example 1):

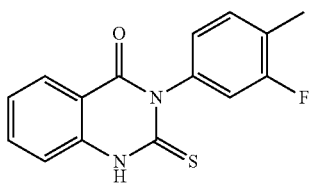 [SMILES: Cc1ccc(-n2c(=S)[nH]c3ccccc3c2=O)cc1F]

In certain non-limiting embodiments, the present invention relates to a compound of Formula IV (corresponding to compound 1-19 of Example 1):

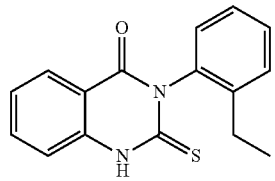 [SMILES: CCc1ccccc1-n1c(=S)[nH]c2ccccc2c1=O]

In certain non-limiting embodiments, the present invention relates to a compound of Formula V (corresponding to compound 1-4 of Example 1):

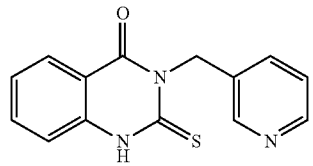 [SMILES: O=c1c2ccccc2[nH]c(=S)n1Cc1cccnc1]

In certain non-limiting embodiments, the present invention relates to a compound of Formula VI (corresponding to compound 1-30 of Example 1):

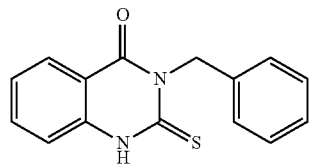 [SMILES: O=c1c2ccccc2[nH]c(=S)n1Cc1ccccc1]

In certain non-limiting embodiments, the present invention relates to a compound of Formula VII (corresponding to compound 1-6 of Example 1):

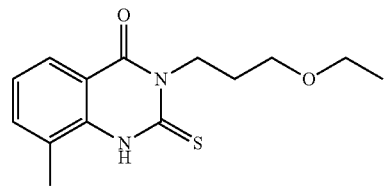 [SMILES: CCOCCCn1c(=S)[nH]c2c(C)cccc2c1=O]

or an analog thereof with a fluorinated or partially fluorinated side chain.

In certain non-limiting embodiments, the present invention relates to a compound of Formula VIII (corresponding to compound 1-8 of Example 1):

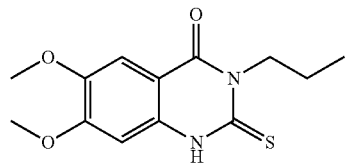 [SMILES: CCCn1c(=S)[nH]c2cc(OC)c(OC)cc2c1=O]

In certain non-limiting embodiments, the present invention relates to a compound of Formula IX (corresponding to compound 2-7 of Example 1):

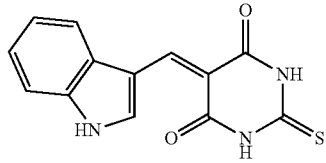 [SMILES: O=C1NC(=S)NC(=O)C1=Cc1c[nH]c2ccccc12]

In certain non-limiting embodiments, the present invention relates to a compound of Formula X (corresponding to compound 2-19 of Example 1):

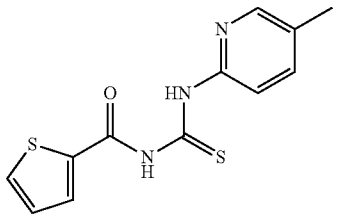 [SMILES: Cc1ccc(NC(=S)NC(=O)c2cccs2)nc1]

In certain non-limiting embodiments, the present invention relates to a compound of Formula XI (corresponding to compound 2-32 of Example 1):

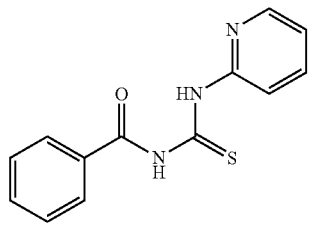 [SMILES: O=C(NC(=S)Nc1ccccn1)c1ccccc1]

In certain non-limiting embodiments, the present invention relates to a compound of Formula XII:

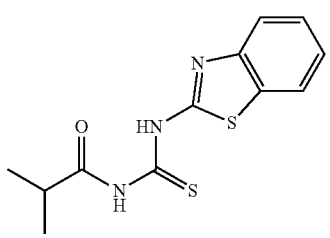 [SMILES: CC(C)C(=O)NC(=S)Nc1nc2ccccc2s1]

or an analog thereof with a chlorine side chain.

In certain non-limiting embodiments, the present invention relates to a compound of Formula XIII (corresponding to compound 2-33 of Example 1):

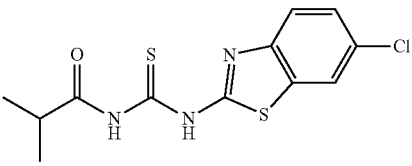 [SMILES: CC(C)C(=O)NC(=S)Nc1nc2ccc(Cl)cc2s1]

In certain non-limiting embodiments, a compound of the present invention can be a salt, ester or prodrug of a compound of any of Formulas I-XIII. For example, and not by way of limitation, a compound of the present invention can be a sodium salt of a compound of any one of Formulas I-XIII.

5.2 Formulations

In certain non-limiting embodiments, the present invention provides for pharmaceutical formulations of the compounds disclosed above for therapeutic use. In certain embodiments, the pharmaceutical formulation can comprise one or more of the disclosed compounds, or salt form thereof, and a pharmaceutically acceptable carrier. In certain embodiments, the pharmaceutical formulation can include a sodium salt form of a disclosed compound. In certain non-limiting embodiments, a pharmaceutical formulation comprises a compound of any of Formulas I-XIII and a pharmaceutically acceptable carrier. In certain particular embodiments, the pharmaceutical formulation can include the compound of Formula II, the compound of Formula IV, the compound of Formula V, the compound of Formula VII and/or the compound of Formula VIII and a pharmaceutically acceptable carrier. In certain particular embodiments, the pharmaceutical formulation can include the compound of Formula VII and a pharmaceutically acceptable carrier. A pharmaceutical formulation of the disclosure can be formulated to be compatible with its intended route of administration, e.g., intravenous, topical, intramuscular, subcutaneous, oral, intraarterial, intraperitoneal, intrathecal, intranasal, pulmonary, vaginal or rectal.

As used herein, the term "pharmaceutically acceptable carrier" refers to any and all solvents, dispersion media, coatings, binders, antibacterial and antifungal agents, isotonic and absorption delaying agents, and the like, compatible with pharmaceutical administration according to the invention. The use of such media and agents for pharmaceutically active substances is well known in the art. In certain embodiments, supplementary active compounds, e.g., second antiproliferative agents, can also be incorporated into the formulations. In certain embodiments, a pharmaceutical formulation contains one or more agents that is/are not an antiproliferative agent but that is beneficial to clinical use of the formulation, for example, but not limiting to, a buffering agent, a stabilizing agent, a preservative, a carrier, etc., as are known in the art.

In certain embodiments, a formulation of the present disclosure includes one or more compounds of any of Formulas I-XIII, together with one or more of the following: sodium chloride, a pharmaceutical buffer, a carrier and a solvent. Non-limiting examples of solvents include water, saline, water-miscible alcohols, dimethylsulfoxide, dimethylacetamide (DMA), ethanol, solutol and mixtures thereof. Non-limiting examples of carriers include albumin (e.g., human serum albumin (HSA)) and cyclodextrin. In certain embodiments, a formulation of the present invention can include a compound of Formula VII and cyclodextrin.

5.3 Agents for Use with the Disclosed Compounds

In certain non-limiting embodiments, one or more compounds of any Formula I-XIII can be used in conjunction with one or more other antiproliferative agents, sometimes referred to herein as a "second antiproliferative agent." Suitable antiproliferative agents include but are not limited to radiation therapy and chemotherapeutic agents. Suitable chemotherapeutic agents include but are not limited to (i) platinum-containing compounds such as cisplatin, carboplatin, oxiplatin and bisplatinate compounds; (ii) other alkylating agents including, but not limited to, carmustine, cyclophosphamide, dacarbazine, Ifosfamide, melphalan and thiotepa; (iii) ATR inhibitors including but not limited to sc-202964, schisandrin B, CGK733, caffeine and ATR inhibitors set forth in Toledo et al. 2011 and/or Reaper et al., 2011; and (iv) Death receptor ligands such as, but not limited to, CD95L, TNFα and TRAIL (TNF-related apoptosis inducing ligand).

In certain embodiments, a formulation of the present invention can include one or compounds of any Formula I-XIII, or salt thereof, and one or more chemotherapeutic agents. For example, but not by way of limitation, the formulation can include one or more compounds of Formulas I-XIII and a platinum-containing compound, e.g., cisplatin or carboplatin. In certain embodiments, a formulation of the present invention can include a compound of Formula VII, or an analog thereof with a fluorinated or partially fluorinated side chain, and cisplatin. In certain embodiments, a formulation of the present invention can include a compound of Formula VII and carboplatin. In certain embodiments, a formulation of the present invention can include a compound of Formula IV and cisplatin or carboplatin.

5.4 Methods of Treatment

The present invention relates to methods for reducing cell proliferation and/or promoting cell death using a compound of any of Formulas I-XIII, alone or in combination with a second antiproliferative agent. It is based, at least in part, on the discovery that in platinum drug-resistant cell lines, certain compounds, together with a second antiproliferative agent (e.g., cisplatin), act synergistically to promote apoptosis.

In certain non-limiting embodiments, cell proliferation is reduced and/or cell death is promoted by at least about 10 percent (for example, cell proliferation is 90 percent or less of a control value and/or cell death is 110 percent or more of a control value), or by least about 20%, by at least about 30%, by at least about 40%, by at least about 50%, by at least about 60%, by at least about 70%, by at least about 80%, by at least about 90%, by at least about 95% or by at least about 98% in the presence of a compound (or a compound and a second antiproliferative agent) relative to proliferation or cell death in the absence of the compound or compounds.

In certain non-limiting embodiments, a synergistic effect, e.g., on cell survival and/or cell death, of at least 10%, of at least about 20%, of at least about 30%, of at least about 40%, of at least about 50%, of at least about 60%, of at least about 70%, of at least about 80%, of at least about 90%, of at least about 100%, of at least about 125%, of at least about 150%, of at least about 175%, of at least about 200%, of at least about 225%, of at least about 250%, of at least about 275%, of at least about 300%, of at least about 325% or of at least about 350% is observed in the presence of a compound and a second antiproliferative agent relative to the sum of the individual effects of the compound and second antiproliferative agent acting alone.

In certain non-limiting embodiments, a synergistic effect observed by the activity of a compound, disclosed herein, and a second antiproliferative agent, can have a combination index (CI) value of less than about 0.8, of less than about 0.7, of less than about 0.6, of less than about 0.5, of less than about 0.4, of less than about 0.3, of less than about 0.2, of less than about 0.1, of less than about 0.05, of less than about 0.025 or of less than about 0.02. In certain embodiments, the CI value is determined based on the method of median-effect principle of Chou and Talalay (Chou, 2010 and Chou, 2006).

In certain non-limiting embodiments, the invention provides for a method for reducing cell proliferation and/or promoting cell death by administering, to a cell, an effective amount of a compound disclosed above. In certain embodiments, a method for reducing cell proliferation and/or promoting cell death includes administering, to a cell, an effective amount of a compound of any of Formulas I-XIII.

In certain embodiments, a chemical compound of any of Formulas I-XIII is administered in combination with an effective amount of a second antiproliferative agent, e.g., a platinum-containing compound. Examples of second antiproliferative agents are provided above in section 5.3.

"In combination with" or "in conjunction with," as used interchangeably herein, mean that a disclosed compound and the second antiproliferative agent are administered to a cell or subject as part of a treatment regimen or plan. These terms do not require that the compound and second antiproliferative agent are physically combined prior to administration nor that they be administered over the same time frame.

As used herein, "an effective amount," refers to an amount that reduces cell proliferation and/or promotes cell death. Where a chemical compound of any of Formulas I-XIII is used in conjunction/combination with a second antiproliferative agent, the amount of each may in some instances be less than an effective amount for that agent taken singly, but when both are used effectiveness is achieved.

In certain non-limiting embodiments, the invention provides for a method for reducing cell proliferation and/or promoting cell death in a subject in need of such treatment comprising administering, to the subject, an effective amount of a compound of any of Formulas I-XIII.

A subject is a human or a non-human subject, such as a primate, dog, cat, horse, cow, pig, sheep, goat, etc.

A "subject in need of such treatment" is a subject suffering from a disorder, or at risk of developing a disorder, where the disorder involves unwanted cell proliferation, including but not limited to neoplastic disorders, cancer (solid and non-solid) and disorders of immunity.

In certain non-limiting embodiments, the method for reducing cell proliferation and/or promoting cell death in a subject in need of such treatment comprising administering, to the subject, an effective amount of a compound of Formula VII, or an analog thereof with a fluorinated or partially fluorinated side chain.

In certain non-limiting embodiments, the method for reducing cell proliferation and/or promoting cell death in a subject in need of such treatment comprising administering, to the subject, an effective amount of a compound of Formula IV.

In certain non-limiting embodiments, the method for reducing cell proliferation and/or promoting cell death in a subject in need of such treatment comprising administering, to the subject, an effective amount of a compound of Formula VIII.

In certain non-limiting embodiments, the invention provides for a method for reducing cell proliferation and/or promoting cell death in a subject in need of such treatment comprising administering, to the subject, an effective amount of a compound of any of Formulas I-XIII in conjunction with a second antiproliferative agent. In certain embodiments, the second antiproliferative agent is cisplatin. In certain embodiments, the second antiproliferative agent is carboplatin.

In certain non-limiting embodiments, the invention provides for a method for reducing cell proliferation and/or promoting cell death in a subject in need of such treatment comprising administering, to the subject, an effective amount of a compound of any of Formulas I-XIII in conjunction with a second antiproliferative agent.

In certain non-limiting embodiments, the method for reducing cell proliferation and/or promoting cell death in a subject in need of such treatment comprising administering, to the subject, an effective amount of a compound of Formula VII, or an analog thereof with a fluorinated or partially fluorinated side chain, in conjunction with a second antiproliferative agent.

In certain non-limiting embodiments, the method for reducing cell proliferation and/or promoting cell death in a subject in need of such treatment comprising administering, to the subject, an effective amount of a compound of Formula IV in conjunction with a second antiproliferative agent.

In certain non-limiting embodiments, the method for reducing cell proliferation and/or promoting cell death in a subject in need of such treatment comprising administering, to the subject, an effective amount of a compound of Formula VIII in conjunction with a second antiproliferative agent.

In certain non-limiting embodiments, the present invention provides for a method of treating a disorder associated with cell proliferation comprising, administering, to a subject in need of such treatment, an effective amount of a compound of any of Formulas I-XIII, optionally in conjunction with a second antiproliferative agent.

In certain non-limiting embodiments, the invention provides for a method for reducing cancer cell proliferation and/or promoting cancer cell death in a subject in need of such treatment comprising administering, to the subject, an effective amount of a compound of any of Formulas I-XIII, optionally in conjunction with a second antiproliferative agent, e.g., cisplatin or carboplatin.

In certain non-limiting embodiments, the present invention provides for a method of treating a cancer in a subject comprising administering, to the subject, an effective amount of a compound of any of Formulas I-XIII, optionally in conjunction with a second antiproliferative agent, e.g., cisplatin or carboplatin. Treating a cancer refers to one or more of the following: reducing the extent or rate of growth of cancer cells or tumor, reducing tumor size, reducing spread of the cancer locally or to other parts of the body, increasing the time interval to relapse (including situations where there is no relapse), increasing survival time and/or increasing survival rate.

In certain non-limiting embodiments, the method of treating a cancer in a subject comprising administering, to the subject, an effective amount of a compound of Formula VII, or an analog thereof with a fluorinated or partially fluorinated side chain, optionally in conjunction with a second antiproliferative agent, e.g., cisplatin or carboplatin.

Cancers and cancer cells, which may be treated according to the invention include, but are not limited to, breast cancer, lung adenocarcinoma, small cell lung cancer, non-small cell lung cancer, mesothelioma, glioblastoma multiforme, melanoma, hepatocarcinoma, pancreatic carcinoma, gastric carcinoma, biliary carcinoma, intestinal carcinoma, colon carcinoma, renal carcinoma, sarcoma, ovarian carcinoma, testicular carcinoma, prostate cancer, bladder cancer, osteosarcoma, squamous cell carcinoma, squamous cell carcinoma of the head and neck, leukemia and lymphoma.

In certain non-limiting embodiments, a compound of the present invention is administered by a route selected from the group consisting of intravenous, topical, intramuscular, subcutaneous, oral, intraarterial, intraperitoneal, intrathecal, intranasal, pulmonary, vaginal or rectal. In certain non-limiting embodiments, a compound of any of Formulas I-XIII is administered intravenously. In certain non-limiting embodiments, a compound of any of Formulas I-XIII is administered via an implant. In certain non-limiting embodiments, a compound of any of Formulas I-XIII is administered by local instillation, for example, at a tumor site or site of tumor resection.

In certain non-limiting embodiments, a second antiproliferative agent, when used, is administered by a route selected from the group consisting of intravenous, intramuscular, subcutaneous, oral, intraarterial, intraperitoneal, intrathecal, intranasal, pulmonary, vaginal or rectal. In certain non-limiting embodiments, a second antiproliferative agent is administered intravenously. In certain non-limiting embodiments, a second antiproliferative agent is administered via an implant. In certain non-limiting embodiments, a second antiproliferative agent is administered by local instillation, for example, at a tumor site or site of tumor resection. In certain embodiments, the compound of the present invention and the second antiproliferative agent can be administered by different administration routes. Alternatively or additionally, the compound of the present invention and the second antiproliferative agent can be administered by the same administration route.

Actual dosage levels of the active ingredients, e.g., the compounds of the present disclosure and/or the second antiproliferative agents, in the pharmaceutical formulations of the present disclosure can be varied so as to obtain an amount of the active ingredient which is effective to achieve the desired therapeutic response for a particular patient, composition and mode of administration, without being toxic to the patient. The selected dosage level will depend upon a variety of pharmacokinetic factors including the activity of the particular compounds of the present disclosure employed, or the ester, salt or amide thereof, the route of administration, the time of administration, the rate of excretion of the particular compound being employed, the duration of the treatment, other drugs, compounds and/or materials used in combination with the particular formulations employed, the age, sex, weight, condition, general health and prior medical history of the patient being treated, and like factors well known in the medical arts.

In a specific non-limiting embodiment, a compound of any of Formulas I-XIII is administered to achieve a local concentration at the site where cell proliferation is to be inhibited of between about 0.001 µM to about 200 µM. In certain embodiments, the local concentration of the compound can be from about 0.1 µM to about 50 µM. In certain embodiments, the local concentration of the compound can be from about 2 µM to about 50 µM.

In a specific non-limiting embodiment where a second antiproliferative agent is administered, the second antiproliferative agent can be administered to achieve a local concentration at the site where cell proliferation is to be inhibited of between about 0.001 µM to 300 µM. In certain embodiments, the local concentration of the second antiproliferative agent can be from about 0.1 µM to about 50 µM. In certain embodiments, the local concentration of the second antiproliferative agent can be about 20 µM or about 200 µM.

In a specific non-limiting embodiment, the second antiproliferative agent is cisplatin, and is administered at a dose of 10-100 mg/m$^2$, administered parenterally, e.g., intravenously.

In a specific non-limiting embodiment, the second antiproliferative agent is carboplatin, and is administered at a dose of 100-400 mg/m$^2$, administered parenterally, e.g., intravenously.

In a specific, non-limiting embodiment, cisplatin or carboplatin is administered with a HSA carrier at a molar ratio of cisplatin (or carboplatin) to HSA of about 1:2.25.

In a specific, non-limiting embodiment, a platinum-containing drug (e.g., cisplatin or carboplatin) is administered with a compound of the present disclosure at a molar ratio of a platinum-containing drug to a compound of the present disclosure from about 20:1 to about 1:1. In certain embodiments, the molar ratio of a platinum-containing drug to a compound of the present disclosure can be from about 4:1 to about 1:1.

5.5 Kits

In certain embodiments, the present disclosure provides kits. In certain embodiments, a kit can include a container, such as a vial, for a formulation comprising a compound of the present disclosure, e.g., a compound of any of Formulas I-XIII, or salt form thereof, in a pharmaceutically acceptable buffer. In a specific non-limiting embodiment, a kit of the present disclosure comprises a compound of Formula VII, in a pharmaceutically acceptable buffer. In certain embodiments, the kit can further include instructions, such as a product insert or label, directing the user to utilize the pharmaceutical formulation for treating a disorder that involves unwanted cell proliferation in a subject.

In certain embodiments, the kit can include a container for a second antiproliferative agent, such as a platinum-containing compound (e.g., cisplatin or carboplatin), for use in combination with a formulation that comprises one or more compounds of any of Formulas I-XIII. Alternatively or additionally, the kit can include a formulation that comprises a compound of the present disclosure and a second antiproliferative agent, and instructions, such as a product insert or label, directing the user to utilize the pharmaceutical formulation for treating a disorder that involves unwanted cell proliferation in a subject. In a specific non-limiting embodiment, a kit of the present disclosure comprises a compound of Formula VII, or an analog thereof with a fluorinated or partially fluorinated side chain, and cisplatin in a pharmaceutically acceptable buffer. In a specific non-limiting embodiment, a kit of the present disclosure comprises a compound of Formula VII and carboplatin in a pharmaceutically acceptable buffer.

6. EXAMPLE 1: SYNERGISTIC PRO-APOPTOTIC EFFECT OF CHEMICAL COMPOUNDS IN COMBINATION WITH PLATINUM AGENTS

In this Example, compounds of the present invention, shown in FIGS. 1-3, were tested to determine their effects on cell viability and survival, alone and in conjunction with other antiproliferative agents.

6.1 Materials and Methods

Reagents.

Mdivi-1 was obtained from Key Organics Ltd (Camelford, Cornwall, UK). Compounds 1-1 to 1-36 and 2-1 to 2-33 are commercially available library components in the University of Pittsburgh Center for Chemical Methodologies and Library Development (UPCMLD) small molecule collection; prior to assaying, compound identities and purities of >92% were ascertained by LC/MS/UV/ELSD analysis. Compound 1-6 of high purity (98%) was obtained from Enatnine Ltd.

Cell Culture.

The cisplatin resistant human ovarian cancer cells A2780cis were obtained from Sigma-Aldrich (St. Louis, Mo.). The human breast carcinoma cell line, MDA-MB-231, and the non-small cell lung carcinoma, H1299, were obtained from American Type Culture Collection (ATCC). LN-428 glioblastoma cells were kindly provided by Dr. Robert W. Sobol (University of Pittsburgh Cancer Institute). Ovarian cancer cells PEO4 were kindly provided by Dr. Karyn J. Hansen (Magee-Womens Hospital of UPMC). Ca133 head and neck cancer cells were kindly provided by Dr. Jennifer R. Grandis (University of Pittsburgh Cancer Institute). Cisplatin sensitive ovarian cancer cells A2780 and their cisplatin resistant derivative cells A2780cis were obtained from Sigma-Aldrich (St. Louis, Mo.). Bax/Bak WT and double knockout MEF cells were established by Dr. Stanley J. Korsmeyer, and kindly provided by Dr. Shivendra Singh (University of Pittsburgh Cancer Institute). Cells were cultured in either RPMI 1640 or DMEM media supplemented with 10% heat-inactivated fetal calf serum and 1% penicillin-streptomycin in 5% $CO_2$ at 37° C.

Cell Proliferation and Cytotoxicity Assay.

Cell proliferation was determined using a CyQUANT Direct Cell Proliferation Assay kit (Invitrogen), the activity of caspase-3/7 was measured using a Caspase-Glo 3/7 Assay Systems (Promega, Madison, Wis.), and the MTS calorimetric survival assay was performed using the CellTiter 96 AQueous One Solution Cell Proliferation Assay kit (Promega, Madison, Wis.), according to the manufacturer's instructions. The survival fractions were calculated after setting untreated control cells at 100%. The data were plotted and curve fitted using GraphPad Prism software. To quantify the number of cells with active caspase-3, cells were fixed with 4% paraformaldehyde (Electron microscopy sciences, Hatfield, Pa.), stained with Alexa Fluor-488 conjugated antibody against cleaved caspase-3 (Asp175) (Cell Signaling Technology, Danvers, Mass.) followed by flow cytometry. An FITC Annexin V Apoptosis Detection Kit (BD PharMingen, San Diego, Calif.) was used to quantify apoptotic cells, according to the manufacturer's instructions.

Extracellular Flux (XF) Analysis.

Oxygen consumption rate (OCR) and extracellular acidification rate (ECAR) were measured as previously described (Qian and Van Houten, 2010). Cells were seeded in XF24 cell culture plates at 4×10$^4$ cells/well and incubated in 5%

$CO_2$ at 37° C. Prior to the analysis, cells were washed and growth medium was replaced with bicarbonate-free modified RPMI 1640 medium, the "assay medium" (Molecular Devices, Sunnyvale, Calif.). Cells were then incubated for another 60 min in a 37° C. incubator without $CO_2$. OCR and ECAR measurements were then performed simultaneously using a Seahorse XF24 Extracellular Flux Analyzer (Seahorse Bioscience, North Billerica, Mass.).

Western Blot Analysis.

Whole cell lysate was prepared by lysing cells in cell lysis buffer (Cell signaling technology) containing complete protease inhibitor (Roche). Cell lysates were then cleared at 15,000 rpm for 15 min at 4° C. The protein content was quantified using a Bio-Rad Protein Assay kit (Bio-Rad Laboratories, Hercules, Calif.). The equal amount of protein was separated on Tris-glycine gels (Invitrogen). The separated proteins were blotted onto a polyvinylidene difluoride membrane and blocked overnight at 4° C. in phosphate-buffered saline containing 0.1% Tween 20 and 10% nonfat dry milk (blocking buffer). Membranes were incubated with primary antibodies in blocking buffer overnight at 4° C. Primary antibodies used were: β-actin from Sigma; Bax, Bak, Caspase-9 and cleaved Caspase-3 from Cell Signaling Technology; phospho-Histone H2AX (Ser 139) and Noxa from Millipore. Membranes were then washed and incubated in peroxidase conjugated anti-rabbit IgG (Sigma) or anti-mouse IgG (Sigma) secondary antibody for 1 h at room temperature. Membranes were developed using SuperSignal West Femto Maximum Sensitivity Substrate (Thermo Fisher Scientific).

Statistical Analysis.

Data were expressed as mean±standard deviation. A Student's t test was used for the comparisons between the treatment with the combination of analogs with cisplatin and with analogs alone. $P<0.05$ was considered statistically significant. Combination index was calculated using CompuSyn software. A value of 0.3-0.7 for the combination index indicates synergism, 0.1-0.3 indicates strong synergism, and <0.1 indicates very strong synergism (Chou, 2006).

6.2 Results

A computational similarity search based on the structure of mdivi-1, an inhibitor of Dynamin-related protein 1 (Drp-1; see FIG. 3), resulted in the identification of 69 structurally related compounds (see FIG. 1 (36 compounds) and FIG. 2 (33 compounds)) in the small molecule library collection of the University of Pittsburgh Center for Chemical Methodologies and Library Development (UPCMLD). The 69 compounds were tested for their activity in combination with the platinum-containing compounds, cisplatin and carboplatin. Of those 69 compounds, 11 compounds, as shown in FIG. 3, were identified as having differential potency in enhancing the efficacy of cisplatin and carboplatin. Further experiments were performed to determine the activity of these compounds in platinum drug resistant cancer cells.

A Caspase-3/7 assay was performed to evaluate the activity of the 36 compounds of FIG. 1 in vitro in the cisplatin-resistant ovarian cancer cell line, A2780cis, alone or in the presence of cisplatin. A microscopic examination of apoptotic morphologic changes was also carried out right before the measurement of Caspase-3/7 activity, in order to confirm that the data on the activation of the Caspase-3/7 following treatment is consistent with morphological change and reflects cell death. Of the 36 compounds shown in FIG. 1, seven (7) compounds were shown to be active in inducing Caspase-3/7 activity, compounds 1-4, 1-6, 1-8, 1-17, 1-19, 1-21 and 1-30 (see Table 1). As shown in Table 2, upon combination treatment of cisplatin with any of the compounds of 1-4, 1-6, 1-8, 1-17, 1-19, 1-21 and 1-30, resulted in an increase in Caspase-3/7 activity as compared to the treatment with cisplatin alone or the compound alone (Table 1).

Of the compounds shown in FIG. 1, all the active compounds contained the 2-thioxo-2,3-dihydroquinazolin-4 (11)-one core. Without being bound to a particular theory, the thioxo group in the pyrimidinone seems to be necessary for bioactivity, since the corresponding quinazoline-2,4(1H, 3H)-diones were inactive. However, the presence of a thiocarbonyl group alone was not sufficient for activity, since all 2-thioxo-2,3-dihydropyrimidin-4(1H)-ones and most 2-thioxo-2,3-dihydroquinazolin-4(1H)-ones were inactive or only weakly active. Electronic effects of substituents in the active samples ranged from mildly electron-withdrawing (1-21) to strongly donating (1-8); strongly electron-withdrawing groups seem to be disfavored (1-16, 1-22 and 1-36). Active compounds all have aromatic or alkyl substituents at N(3), whereas N(1) is unsubstituted. However, bulky, basic, or highly functionalized side chains at N(3) are also not tolerated (1-5, 1-7, 1-9, 1-12, 1-13, 1-14, 1-28 and 1-29). Surprisingly, all five thioxodihydrothienopyrimidinones were inactive, in spite of the similarity of their core structures to the active thioxodihydroquinazolinones, possibly due to the additional large substituents attached or fused to the thiophene ring (1-1, 1-2, 1-3, 1-15 and 1-27).

TABLE 1

Biological data for compounds shown in FIG. 1. Apoptotic cell death was determined by the activity of Caspase-3/7 in the cisplatin-resistant ovarian cancer cell line A2780cis, after treatment for 20 h.

| entry | compound | caspase-3/7 activity (Lum)[a] | |
|---|---|---|---|
| | | compound alone[b] | compound with cisplatin[c] |
| 1 | — | 13 ± 1 | — |
| 2 | cisplatin | 30 ± 1 | — |
| 3 | mdivi-1 | 28 ± 5 | 102 ± 3 |
| 4 | 1-1 | 12 ± 1 | 28 ± 1 |
| 5 | 1-2 | 12 ± 1 | 25 ± 3 |
| 6 | 1-3 | 12 ± 1 | 28 ± 2 |
| 7 | 1-4 | 13 ± 1 | 93 ± 5 |
| 8 | 1-5 | 13 ± 1 | 32 ± 1 |
| 9 | 1-6 | 12 ± 0 | 145 ± 6 |
| 10 | 1-7 | 12 ± 2 | 20 ± 3 |
| 11 | 1-8 | 14 ± 2 | 121 ± 4 |
| 12 | 1-9 | 13 ± 1 | 23 ± 1 |
| 13 | 1-10 | 14 ± 1 | 21 ± 2 |
| 14 | 1-11 | 12 ± 1 | 18 ± 2 |
| 15 | 1-12 | 10 ± 1 | 23 ± 3 |
| 16 | 1-13 | 14 ± 1 | 35 ± 3 |
| 17 | 1-14 | 11 ± 1 | 22 ± 2 |
| 18 | 1-15 | 12 ± 2 | 28 ± 3 |
| 19 | 1-16 | 10 ± 1 | 18 ± 3 |
| 20 | 1-17 | 10 ± 2 | 123 ± 5 |
| 21 | 1-18 | 12 ± 1 | 19 ± 3 |
| 22 | 1-19 | 12 ± 1 | 136 ± 12 |
| 23 | 1-20 | 13 ± 1 | 39 ± 3 |
| 24 | 1-21 | 17 ± 3 | 90 ± 6 |
| 25 | 1-22 | 16 ± 1 | 25 ± 2 |
| 26 | 1-23 | 15 ± 1 | 27 ± 1 |
| 27 | 1-24 | 13 ± 1 | 25 ± 2 |
| 28 | 1-25 | 15 ± 1 | 33 ± 2 |
| 29 | 1-26 | 14 ± 3 | 26 ± 1 |
| 30 | 1-27 | 23 ± 2 | 40 ± 5 |
| 31 | 1-28 | 15 ± 1 | 22 ± 2 |
| 32 | 1-29 | 15 ± 2 | 23 ± 1 |
| 33 | 1-30 | 18 ± 2 | 111 ± 8 |
| 34 | 1-31 | 12 ± 1 | 26 ± 4 |

TABLE 1-continued

Biological data for compounds shown in FIG. 1. Apoptotic cell death was determined by the activity of Caspase-3/7 in the cisplatin-resistant ovarian cancer cell line A2780cis, after treatment for 20 h.

| | | caspase-3/7 activity (Lum)[a] | |
|---|---|---|---|
| entry | compound | compound alone[b] | compound with cisplatin[c] |
| 35 | 1-32 | 13 ± 1 | 20 ± 1 |
| 36 | 1-33 | 10 ± 1 | 16 ± 1 |
| 37 | 1-34 | 12 ± 1 | 22 ± 3 |
| 38 | 1-35 | 2 ± 1 | 5 ± 1 |
| 39 | 1-36 | 16 ± 2 | 47 ± 3 |

[a]Data represents the mean ± S.D. of triplicates.
[b]Compound tested at 20 μM.
[c]Compound tested at 20 μM with 20 μM cisplatin.

After identifying the thiourea function as a necessary requirement, another 33 compounds with structural features of an acyclic acyl thiourea core or a 2-thioxo-2,3-dihydro-pyrimidin-4(1H)-one (thiobarbiturate) moiety (FIG. 2) were selected from the same small molecule library collection used to select the compounds shown in FIG. 1. The same screening method used for the compounds shown in FIG. 1 was used to evaluate activity of the compounds in FIG. 2. In this series, compounds 2-7, 2-19, 2-32 and 2-33 were found to be active (see Tables 3 and 4). Compounds 2-32 and 2-33 were initially identified through the microscopic observation of cell morphology changes after treatment. Without being bound to a particular theory, the lack of activity of these two compounds in the Caspase-3/7 activity assay while showing a positive response in the CellTiter-Blue cell viability assay may be due to their interference with the Caspase-3/7 activity assay system. In spite of the low hit rate, some useful information was obtained from this screen. For example, the majority of the thioureas were inactive, and among the few that showed an effect (2-19, 2-32 and 2-33), the presence of a nitrogen-containing heterocycle attached to the terminal thiourea nitrogen was noteworthy (but not sufficient, e.g., 2-23 and 2-24 were closely related inactive compounds). Without being bound to a particular theory, the steric and electronic effects of both substituents attached to the nitrogens of the thiourea core appear to be important for activity (i.e., 2-19 versus 2-2 and 2-23). The thiobarbiturates were all inactive with the exception of 2-7. Based on the data obtained by studying the antiproliferative activity of the compounds shown in FIGS. 1 and 2, a pharmacophore model was generated (FIG. 10). As shown in FIG. 10, the heterocyclic core can contain a thiourea moiety, and N-substitution by electron-rich aromatic substituents is preferred. The most active compounds also contain a fused benzene ring.

TABLE 2

| | | Caspase-3/7 activity (Lum)[a] | |
|---|---|---|---|
| Entry | Compound | Compound alone[b] | Compound with cisplatin[c] |
| 1 | — | 13 ± 1 | — |
| 2 | Cisplatin | 30 ± 1 | — |
| 3 | Mdivi-1 | 28 ± 5 | 102 ± 3 |
| 4 | 1-4 | 13 ± 1 | 93 ± 5 |
| 5 | 1-6 | 12 ± 0 | 145 ± 6 |
| 6 | 1-8 | 14 ± 2 | 121 ± 4 |
| 7 | 1-17 | 10 ± 2 | 123 ± 5 |
| 8 | 1-19 | 12 ± 1 | 136 ± 12 |

TABLE 2-continued

| | | Caspase-3/7 activity (Lum)[a] | |
|---|---|---|---|
| Entry | Compound | Compound alone[b] | Compound with cisplatin[c] |
| 9 | 1-21 | 17 ± 3 | 90 ± 6 |
| 10 | 1-30 | 18 ± 2 | 111 ± 8 |

Apoptotic cell death was determined by the activity of caspase-3/7 in the cisplatin-resistant ovarian cancer cell line A2780cis, after treatment for 20 h.
[a]Data represents the mean ± SD of triplicates.
[b]Compound tested at 20 μM.
[c]Compound tested at 20 μM in the presence of 20 μM cisplatin.

TABLE 3

Biological data for the compounds shown in FIG. 2. Apoptotic cell death was determined by the activity of caspase-3/7 in the cisplatin-resistant ovarian cancer cell line A2780cis, after treatment for 20 h.

| | | caspase-3/7 activity (Lum)[a] | |
|---|---|---|---|
| entry | compound | compound alone[b] | compound with cisplatin[c] |
| 1 | — | 8 ± 2 | — |
| 2 | cisplatin | 35 ± 4 | — |
| 3 | mdivi-1 | 20 ± 3 | 80 ± 11 |
| 4 | 2-1 | 10 ± 2 | 27 ± 2 |
| 5 | 2-2 | 9 ± 1 | 25 ± 1 |
| 6 | 2-3 | 8 ± 1 | 20 ± 1 |
| 7 | 2-4 | 8 ± 1 | 18 ± 1 |
| 8 | 2-5 | 9 ± 1 | 19 ± 2 |
| 9 | 2-6 | 7 ± 1 | 22 ± 1 |
| 10 | 2-7 | 25 ± 1 | 41 ± 3 |
| 11 | 2-8 | 7 ± 2 | 20 ± 2 |
| 12 | 2-9 | 8 ± 1 | 20 ± 2 |
| 13 | 2-10 | 7 ± 2 | 20 ± 2 |
| 14 | 2-11 | 9 ± 1 | 17 ± 2 |
| 15 | 2-12 | 7 ± 1 | 18 ± 1 |
| 16 | 2-13 | 8 ± 1 | 20 ± 3 |
| 17 | 2-14 | 8 ± 1 | 21 ± 2 |
| 18 | 2-15 | 8 ± 1 | 18 ± 3 |
| 19 | 2-16 | 8 ± 1 | 17 ± 1 |
| 20 | 2-17 | 7 ± 2 | 18 ± 1 |
| 21 | 2-18 | 9 ± 1 | 17 ± 1 |
| 22 | 2-19 | 9 ± 1 | 50 ± 8 |
| 23 | 2-20 | 8 ± 1 | 15 ± 2 |
| 24 | 2-21 | 8 ± 1 | 25 ± 1 |
| 25 | 2-22 | 9 ± 1 | 26 ± 2 |
| 26 | 2-23 | 7 ± 0 | 22 ± 2 |
| 27 | 2-24 | 7 ± 1 | 19 ± 5 |
| 28 | 2-25 | 6 ± 0 | 24 ± 2 |
| 29 | 2-26 | 6 ± 0 | 21 ± 4 |
| 30 | 2-27 | 7 ± 1 | 19 ± 3 |
| 31 | 2-28 | 7 ± 1 | 18 ± 2 |
| 32 | 2-29 | 7 ± 1 | 19 ± 3 |
| 33 | 2-30 | 6 ± 0 | 20 ± 5 |
| 34 | 2-31 | 2 ± 1 | 6 ± 2 |
| 35 | 2-32 | 0 ± 1 | 4 ± 1 |
| 36 | 2-33 | 11 ± 2 | 23 ± 3 |

[a]Data represents the mean ± S.D. of triplicates.
[b]Compound tested at 20 μM.
[c]Compound tested at 20 μM with 20 μM of cisplatin.

TABLE 4

| | | Caspase-3/7 activity (Lum)[a] | |
|---|---|---|---|
| Entry | Compound | Compound alone[b] | Compound with cisplatin[c] |
| 1 | — | 8 ± 2 | — |
| 2 | Cisplatin | 35 ± 4 | — |
| 3 | Mdivi-1 | 20 ± 3 | 80 ± 11 |
| 4 | 2-7 | 25 ± 1 | 41 ± 3 |
| 5 | 2-19 | 9 ± 1 | 50 ± 8 |

TABLE 4-continued

| | | Caspase-3/7 activity (Lum)[a] | |
|---|---|---|---|
| Entry | Compound | Compound alone[b] | Compound with cisplatin[c] |
| 6 | 2-32[d] | 0 ± 1 | 4 ± 1 |
| 7 | 2-33[d] | 11 ± 2 | 23 ± 3 |

Apoptotic cell death was determined by the activity of caspase-3/7 in the cisplatin-resistant ovarian cancer cell line A2780cis, after treatment for 20 h.
[a]Data represent the mean ± SD of tripiicates.
[b]Compound tested at 20 μM.
[c]Compound tested at 20 μM with 20 μM of cisplatin.
[d]The lack of activity is probably due to the interference of the analogs with the caspase-3/7 activity assay system.

To further validate the activity of the identified 11 active compounds (see FIG. 3), a CellTiter-Blue cell viability assay was performed with increasing concentrations (10 μM, 20 μM and 50 μM) of the disclosed compounds (see FIG. 4 and Table 5). Cisplatin resistant ovarian cancer cells (A2780cis) were treated with a disclosed compound alone, cisplatin alone or a combination of a compound with cisplatin for 24 h to determine the effects of the compounds on cell viability. Cell viability was reduced after the combination treatment of cisplatin (20 μM) with any of the indicated compounds compared to the treatment with cisplatin or compound alone. These results indicate that these compounds can enhance the efficacy of cisplatin, and the combination of cisplatin with these compounds produces a synergistic anti-proliferative effect. In particular, compounds 1-6, 1-8, 1-17 and 1-19 were more potent than mdivi-1 at enhancing the cytotoxicity of cisplatin, as indicated by the larger reduction in cell viability observed when cisplatin was combined with these compounds at 10 μM compared to mdivi-1 at 10 μM (FIG. 4). Consistent with the cell viability results (FIG. 4), the combination of cisplatin with 1-6, 1-8, 1-17, and 1-19 was also more effective in the activation of Caspase-3/7 when compared to mdivi-1 (FIG. 7A and Table 6).

Further analysis was performed with compound 1-6. In order to quantify the combination effect, the combination index (CI) was calculated for the most active compound, compound 1-6, based on the method of median-effect principle of Chou and Talalay (Chou, 2010 and Chou, 2006). As shown in Table 7, the combination of cisplatin and compound 1-6 produced a synergistic effect ranging from synergism to very strong synergism depending on the concentration of 1-6. This synergism for the combination of cisplatin and 1-6 was further confirmed using a fresh sample of high chemical purity (98%). This synergistic effect was also observed using the CellTiter-Blue cell viability assay (FIG. 5) under an alternative exposure strategy that mimics in viva drug administration to test the combination effect. Considering the clearance of cisplatin over the time and the duration of exposure of tumor cells to the effective doses of the drugs in vivo (Los et al., 1989), a short-term exposure of cells to the combination of 20 μM of 1-6 with various doses of cisplatin was tested, followed by cell viability assay after two days. It was found that a 3 hr exposure of the cells to the combination of cisplatin and 1-6 was sufficient to cause a severe long-term proliferation defect, as compared to the treatment with cisplatin alone, which only had a slight effect on cell viability (FIG. 5). As shown in FIG. 5, the combination of compound 1-6 with cisplatin resulted in a synergistic effect on cell survival compared to cisplatin alone.

TABLE 5

Synergistic cytotoxicity of various concentrations of active compounds in combination with cisplatin. Cell viability was determined by a CellTiter-Blue assay in the cisplatin-resistant ovarian cancer cell line A2780cis, after treatment for 24 h.

| | | survival (%) of cells with compound alone [a] | | | survival (%) [a] of cells with compound and cisplatin (20 μM) | | |
|---|---|---|---|---|---|---|---|
| entry | compound | 10 μM | 20 μM | 50 μM | 10 μM | 20 μM | 50 μM |
| 1 | cisplatin | — | 89.3 ± 0.6 | — | — | — | — |
| 2 | mdivi-1 | 98.4 ± 2.4 | 78.4 ± 3.8 | 61.6 ± 4.4 | 87.4 ± 2.9 | 39.2 ± 2.7 | 26.3 ± 3.4 |
| 3 | 1-4 | 95.9 ± 2.4 | 95.6 ± 1.3 | 91.8 ± 2.9 | 89.8 ± 0.1 | 61.2 ± 3.4 | 20.9 ± 1.3 |
| 4 | 1-6 | 98.9 ± 3.1 | 95.4 ± 4.2 | 93.7 ± 4.4 | 58.8 ± 1.5 | 28.0 ± 1.6 | 1.5 ± 0.6 |
| 5 | 1-8 | 99.6 ± 2.9 | 96.3 ± 3.2 | 88.4 ± 2.1 | 53.4 ± 1.5 | 25.9 ± 2.3 | 17.9 ± 1.3 |
| 6 | 1-17 | 100.6 ± 2.9 | 100.9 ± 2.1 | 101.4 ± 1.4 | 63.0 ± 1.1 | 39.6 ± 3.0 | 26.7 ± 1.4 |
| 7 | 1-19 | 102.9 ± 1.2 | 99.6 ± 3.0 | 98.5 ± 1.7 | 47.9 ± 4.8 | 25.3 ± 1.0 | 4.9 ± 1.4 |
| 8 | 1-21 | 102.5 ± 1.4 | 100.4 ± 1.5 | 84.9 ± 2.9 | 90.8 ± 1.4 | 63.1 ± 6.8 | 26.7 ± 2.0 |
| 9 | 1-30 | 95.0 ± 2.6 | 95.4 ± 0.9 | 98.1 ± 0.9 | 73.4 ± 6.9 | 52.4 ± 1.2 | 53.2 ± 5.0 |
| 10 | 2-7 | 97.0 ± 1.5 | 93.3 ± 3.6 | 47.2 ± 1.8 | 91.9 ± 14.0 | 76.1 ± 6.6 | 39.4 ± 5.2 |
| 11 | 2-19 | 97.3 ± 1.8 | 95.9 ± 2.1 | 95.1 ± 6.4 | 100.4 ± 1.2 | 85.4 ± 9.6 | 53.2 ± 16.0 |
| 12 | 2-32 | 97.2 ± 2.9 | 96.0 ± 1.7 | 81.8 ± 5.2 | 102.7 ± 3.9 | 64.9 ± 10.6 | 33.4 ± 11.8 |
| 13 | 2-33 | 84.8 ± 4.1 | 77.9 ± 1.1 | 65.0 ± 6.4 | 92.5 ± 4.8 | 70.4 ± 4.9 | 58.6 ± 7.4 |

[a] Data represent the mean ± S.D. of triplicates. Concentrations refer to the tested compound. Untreated cells are at 100% survival.

TABLE 6

Combination of various concentrations of potent compounds with cisplatin induces apoptotic cell death as determined by the activity of caspase-3/7 in the cisplatin-resistant ovarian cancer cell line A2780cis, after treatment for 20 h.

| entry | compound | caspase-3/7 activity (Lum) with compound alone [a] | | | caspase-3/7 activity (Lum) with compound and cisplatin (20 μM) [a] | | |
|---|---|---|---|---|---|---|---|
| | | 5 μM | 10 μM | 20 μM | 5 μM | 10 μM | 20 μM |
| 1 | cisplatin | — | — | 28 ± 4 | — | — | — |
| 2 | mdivi-1 | 10 ± 1 | 10 ± 1 | 24 ± 2 | 22 ± 2 | 24 ± 3 | 84 ± 3 |
| 4 | 1-6 | 10 ± 1 | 10 ± 1 | 11 ± 2 | 22 ± 1 | 67 ± 3 | 105 ± 7 |
| 5 | 1-8 | 10 ± 1 | 10 ± 1 | 11 ± 1 | 38 ± 4 | 72 ± 1 | 93 ± 4 |
| 6 | 1-17 | 15 ± 8 | 10 ± 1 | 10 ± 1 | 34 ± 3 | 76 ± 7 | 101 ± 6 |
| 7 | 1-19 | 9 ± 2 | 8 ± 1 | 9 ± 1 | 36 ± 3 | 114 ± 5 | 96 ± 11 |

[a] Data represent the mean ± S.D. of triplicates. Concentrations refer to the tested compound. Untreated cells are at a Lum value of 9 ± 1.

TABLE 7

Combination index (CI) for the combination of the most active compound, compound 1-6, with cisplatin (20 μM).

| | Compound 1-6 | | |
|---|---|---|---|
| | 10 μM | 20 μM | 50 μM |
| Combination Index | 0.67 | 0.24 | 0.01 |
| Grading | Synergism | Strong synergism | Very strong synergism |

CI was calculated using CompuSyn software.

Analysis of the effect of the disclosed compounds with another platinum-containing compound, carboplatin, was performed. A2780cis cells were treated with carboplatin alone or with the combination of carboplatin and the disclosed compounds at indicated concentrations for 24 h followed by the analysis of cell viability. As shown in FIG. 6, cell viability was reduced after combination treatment with compounds 1-6, 1-8, 1-17 and 1-19 and carboplatin compared to carboplatin alone, indicating that these compounds can enhance the efficacy of carboplatin. Greater reductions in cell viability were observed at higher concentrations of the compounds in combination with carboplatin (FIG. 6 and Table 8).

Further experiments were performed to determine the mechanism of action of the four most potent compounds 1-6, 1-8, 1-17 and 1-19 when combined with cisplatin. A2780cis cells were treated with cisplatin alone, compounds alone or in combination with cisplatin at indicated concentrations for 20 h to analyze apoptotic cell death in response to treatment. As shown in FIG. 7A, compounds 1-6, 1-8, 1-17 and 1-19 were more potent than mdivi-1 in enhancing the efficacy of cisplatin, as indicated by the significant increase in Caspase 3/7 activity in the presence of the compound in combination with cisplatin compared to the combination of cisplatin and mdivi-1. Expression and cleavage of several major caspases (Caspase-8, Caspase-9 and Caspase-3), as well as poly (ADP-ribose) polymerase (PARP) and NOXA. A2780cis cells were treated with cisplatin (20 μM) alone, compounds (20 μM) alone or in combination with cisplatin for 20 h. As shown in FIG. 7B, compounds 1-6, 1-8, 1-17 and 1-19, in combination with cisplatin, resulted in the cleavage of Caspase-8, 9, 3, PARP and the induction of Noxa similar to mdivi-1, in combination with cisplatin, as compared to the compounds alone.

To determine the effects of the compounds on DNA damage and mitochondrial dysfunction, A2780cis cells were treated with cisplatin (20 μM) alone or the combination of cisplatin with 20 μM of compound 1-6. Replication protein A (RPA) is a single strand-specific DNA-binding protein, consisting of three subunits, RPA70, RPA32, and RPA14. RPA32 is phosphorylated in response to DNA replication stress. Western blot analysis was performed to evaluate the phosphorylation of RPA32 and histone H2AX, the induction of Noxa expression and cleavage of caspase-3. The combination of cisplatin and compound 1-6 enhanced the phosphorylation of RPA32 as early as 4 h post treatment, whereas treatment with cisplatin alone showed an increase in the phosphorylation of RPA32 only after 12 h post treatment. Both the phosphorylation of RPA32 and upregulation of Noxa occurred earlier than the phosphorylation of H2AX and cleavage of caspase-3, indicating that the replication stress and activation of mitochondrial apoptotic pathway are primary events following the combination treatment (FIG. 8A). Further analysis was performed to determine if compound 1-6, in combination with cisplatin, resulted in the dysfunction of the mitochondria. A2780cis cells were treated with cisplatin (50 μM) alone, 1-6 (50 μM) alone or the combination of cisplatin and compound 1-6 for 4 h. The oxygen consumption rate (OCR) was measured by a Seahorse extracellular flux analyzer. As shown in FIG. 8B, the uncoupling of mitochondria was observed after combination treatment with cisplatin and compound 1-6 and not after treatment with the agents alone, as indicated by the lack of response to oligomycin-mediated inhibition of OCR following combination treatment.

In order to understand the role of Bax and Bak in the efficacy of cisplatin and compound 1-6, Bax/Bak double knockout (DKO) SV40-transformed MEF cells were used. Bax/Bak wildtype (WT) and DKO MEF cells were treated with cisplatin (10 μM) alone, or the combination with mdivi-1 (20 μM) or compound 1-6 (20 μM) for 20 h. cleavage of Caspase-8, 9, and 3 were determined by western blot. As shown in FIG. 8C, the combination of cisplatin and compound 1-6 results in the cleavage of Caspase 3 and 9 independent of Bax or Bak activity.

To evaluate whether the synergistic effects of the disclosed compounds and cisplatin could be extended to other types of cancer cells, breast cancer cells (MDA-MB-231), non-small cell lung carcinoma cells (H-1299), ovarian cancer cells (PEO4 and SKOV3) and head and neck cancer cells (Ca133) were treated with various combinations of cisplatin and compound 1-6 and analyzed for Caspase-3. As shown in FIG. 9, cleavage of Caspase 3 and PARP was observed between compound 1-6 and cisplatin in various types of cancer cells. Single compound exposure was found to have minimal effect in inducing cell death in these cells.

TABLE 8

Synergistic cytotoxicity of various concentrations of active compounds in combination with carboplatin

| | | Survival (%)$^a$ of cells with compound and carboplatin (200 μM) | | |
|---|---|---|---|---|
| Entry | Compound | 10 μM | 20 μM | 50 μM |
| 1 | Mdivi-1 | 92.6 ± 3.5 | 75.1 ± 3.9 | 40.6 ± 3.0 |
| 2 | 1-6 | 64.5 ± 2.7 | 48.0 ± 3.0 | 2.5 ± 0.4 |
| 3 | 1-8 | 89.5 + 2.1 | 65.8 ± 3.5 | 42.5 ± 2.3 |
| 4 | 1-17 | 90.7 ± 0.9 | 79.3 ± 3.9 | 69.7 ± 4.1 |
| 5 | 1-19 | 103.5 ± 1.6 | 70.0 ± 2.9 | 31.6 ± 4.2 |

Cell viability was determined by a CellTiter-Blue assay in the cisplatin-resistant ovarian cancer cell line A2780cis, after treatment for 24 h.
$^a$Data represent the mean ± SD of triplicates. Concentrations refer to the tested compound. Untreated cells are at 100% survival and cells treated with carboplatin alone (200 μM) are at 99.6% survival.

6.3 Discussion

In this Example, it is shown that the disclosed compounds, when combined with cisplatin or carboplatin, are able to efficiently overcome platinum drug resistance and produce a synergistic effect on cell survival compared to cisplatin alone. Without being limited to a particular theory, it appears that the disclosed compounds function by the same mechanism of action as mdivi-1 when combined with cisplatin, including enhanced replication stress, mitochondrial dysfunction and Bax/Bak-independent mitochondrial apoptosis. The testing of the new compounds was mainly performed in platinum and multidrug resistant ovarian cancer cells; however, the potency of these compounds with the combination of cisplatin were observed in other types of cancers such as lung, breast and head and neck cancers.

7. REFERENCES

Andrews, P. A., and S. B. Howell. 1990. Cellular pharmacology of cisplatin: perspectives on mechanisms of acquired resistance. Cancer Cells. 2:35-43.

Chou, T. C. Cancer Res. 2010, 70:440.

Chou, T. C. Pharmacol. Rev. 2006, 58:621

Galluzzi, L., L. Senovilla, I. Vitale, J. Michels, I. Martins, O. Kepp, M. Castedo, and G. Kroemer. 2012. Molecular mechanisms of cisplatin resistance. Oncogene. 31:1869-1883.

Mullany, L. K., and J. S. Richards. 2012. Minireview: animal models and mechanisms of ovarian cancer development. Endocrinology. 153:1585-1592.

Qian, W., S. Choi, G. A. Gibson, S. C. Watkins, C. J. Bakkenist, and B. Van Houten. 2012. Mitochondrial hyperfusion induced by loss of the fission protein Drp1 causes ATM-dependent G2/M arrest and aneuploidy through DNA replication stress. J Cell Sci. 125:5745-5757.

Qian, W., Wang, J., Roginskaya, V., McDermott, L., Edwards, R., Stolz, D., Llambi, F., Green, D., Van Houten, B. 2014. Novel combination of mitochondrial division inhibitor 1 (mdivi-1) and platinum agents produces synergistic pro-apoptotic effect in drug resistant tumor cells. Oncotarget 5(12):4180-94.

Qian W and Van Houten B. Alterations in bioenergetics due to changes in mitochondrial DNA copy number. Methods. 2010; 5I(4):452-457.

Romero, I., and R. C. Bast, Jr. 2012. Minireview: human ovarian cancer: biology, current management, and paths to personalizing therapy. Endocrinology. 153:1593-1602.

Runowicz, C. D. 1992. Advances in the screening and treatment of ovarian cancer. CA: a cancer journal for clinicians. 42:327-349.

Stewart, J. J., J. T. White, X. Yan, S. Collins, C. W. Drescher, N. D. Urban, L. Hood, and B. Lin. 2006. Proteins associated with Cisplatin resistance in ovarian cancer cells identified by quantitative proteomic technology and integrated with mRNA expression levels. Mol Cell Proteornics. 5:433-443.

Wang, C., and R. J. Youle. 2012. Predominant requirement of Bax for apoptosis in HCT116 cells is determined by Mcl-1's inhibitory effect on Bak. Oncogene. 31:3177-3189.

Wang, D., and S. J. Lippard. 2005. Cellular processing of platinum anticancer drugs. Nature reviews. Drug discovery. 4:307-320.

Publications are cited throughout this application, the disclosures of which are incorporated herein by reference in their entireties for all purposes.

We claim:

1. A method for reducing cancer cell proliferation and/or promoting cancer cell death by administering, to a cancer cell, an effective amount of a compound having a formula selected from the group consisting of Formula I:

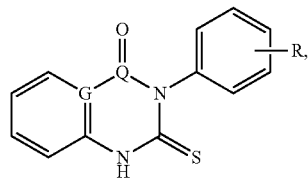

wherein G is C; Q is C; and R is selected from H, a substituted or unsubstituted alkyl, a fluorinated or partially fluorinated alkyl, a halogen, cyano, azido, hydroxyl, a substituted or unsubstituted sulfonyl;

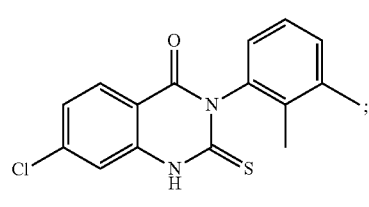

Formula II

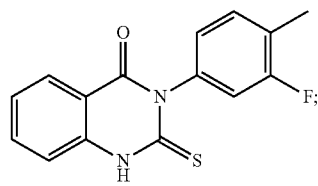

Formula III

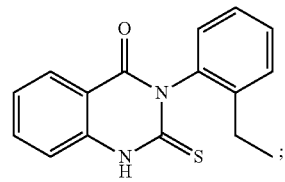

Formula IV

-continued

Formula V
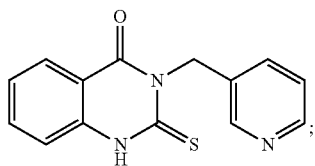

Formula VI
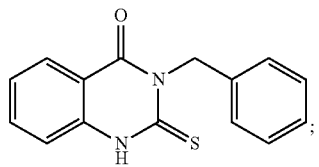

Formula VII
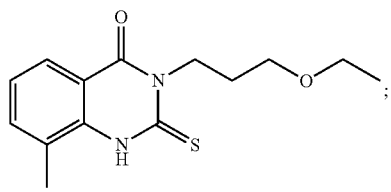

Formula VIII
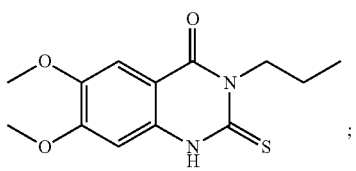

Formula X
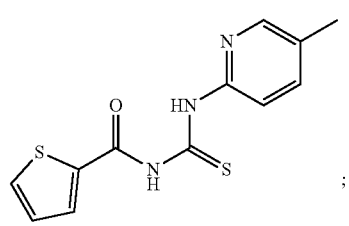

Formula XI
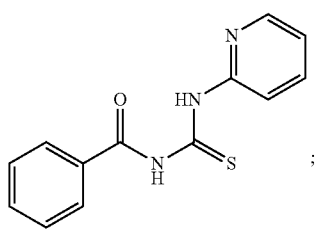

Formula XII
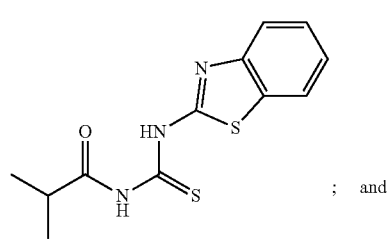

; and

Formula XIII
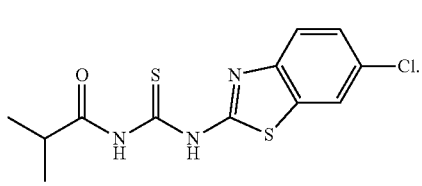

2. The method of claim 1, further comprising administering, to the cancer cell, an effective amount of a second antiproliferative agent.

3. The method of claim 2, wherein the second antiproliferative agent is a platinum compound.

4. The method of claim 3, wherein the platinum compound is cisplatin.

5. The method of claim 3, wherein the platinum compound is carboplatin.

6. A method for reducing cancer cell proliferation and/or promoting cancer cell death in a subject in need of such treatment comprising administering, to the subject, an effective amount of a compound having a formula selected from the group consisting of Formula I:

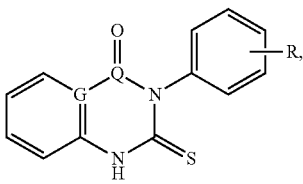

wherein G is C; Q is C; and R is selected from H, a substituted or unsubstituted alkyl, a fluorinated or partially fluorinated alkyl, a halogen, cyano, azido, hydroxyl, a substituted or unsubstituted sulfonyl;

Formula II
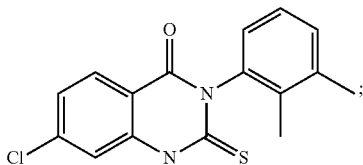

Formula III
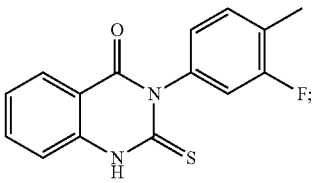

Formula IV
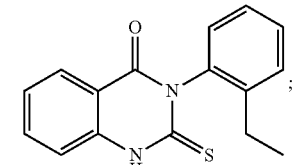

Formula V
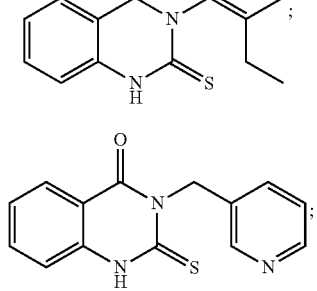

Formula VI
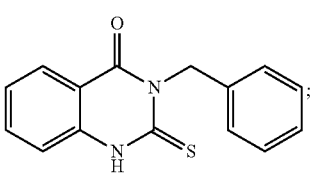

-continued

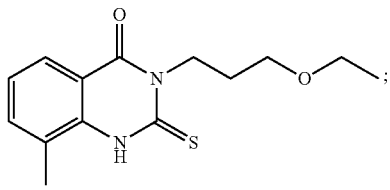

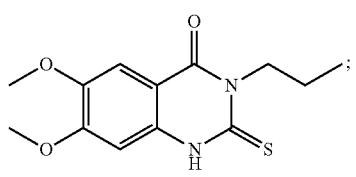

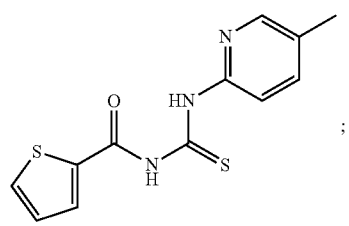

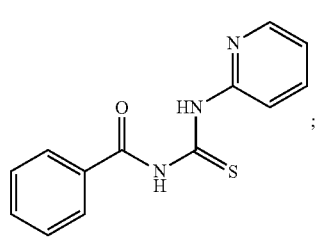

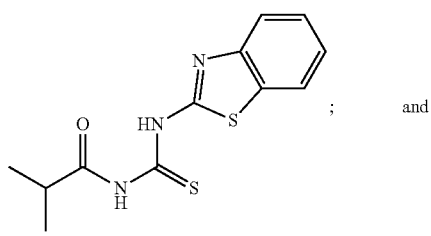

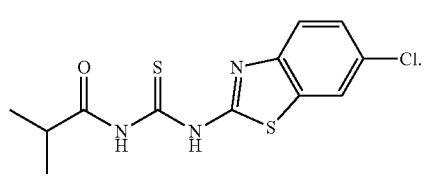

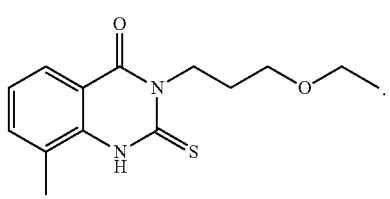 [SMILES: CCOCCCn1c(=S)[nH]c2c(C)cccc2c1=O]

Formula VII

Formula VIII

Formula X

Formula XI

Formula XII

Formula XIII

7. The method of claim 6, wherein the compound is a compound having the Formula VII 8. The method of claim 6, wherein the compound is a compound having the Formula II

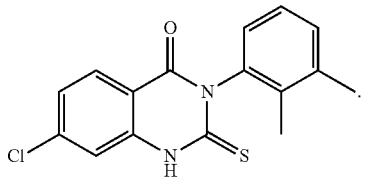 [SMILES: Cc1cccc(-n2c(=S)[nH]c3cc(Cl)ccc3c2=O)c1C]

9. The method of claim 6, wherein the compound is a compound having the Formula IV

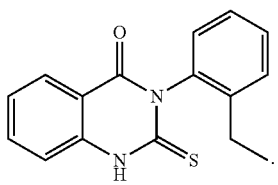 [SMILES: CCc1ccccc1-n1c(=S)[nH]c2ccccc2c1=O]

10. The method of claim 6, wherein the compound is a compound having the Formula V

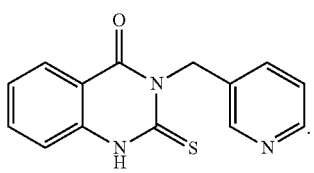 [SMILES: O=c1c2ccccc2[nH]c(=S)n1Cc1cccnc1]

11. The method of claim 6, wherein the compound is a compound having the Formula VIII

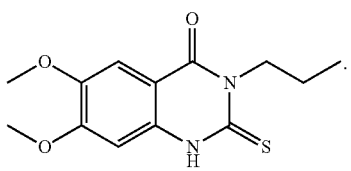 [SMILES: CCCn1c(=S)[nH]c2cc(OC)c(OC)cc2c1=O]

12. The method of claim 6, wherein the cancer is selected from the group consisting of breast cancer, lung cancer, ovarian cancer, glioblastoma, squamous cell carcinoma of the head and neck, melanoma and colon cancer.

13. The method of claim 6, further comprising administering, to the subject, an effective amount of a second antiproliferative agent.

14. The method of claim 13, wherein the second antiproliferative agent is a platinum compound.

15. The method of claim 14, wherein the platinum compound is cisplatin.

16. The method of claim 14, wherein the platinum compound is carboplatin.

17. The method of claim 6, wherein the cancer is breast cancer.

18. The method of claim 6, wherein the cancer is lung cancer.

19. The method of claim 6, wherein the cancer is ovarian cancer.

20. The method of claim 6, wherein the cancer is glioblastoma.

21. The method of claim 6, wherein the cancer is squamous cell carcinoma of the head and neck.

22. The method of claim 6, wherein the cancer is melanoma.

23. The method of claim 6, wherein the cancer is colon cancer.

24. A pharmaceutical formulation comprising an effective amount of a compound for reducing cancer cell proliferation and/or promoting cancer cell death, having a formula selected from the group consisting of Formula I:

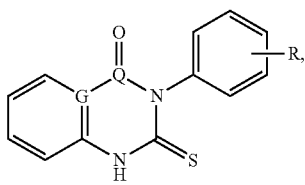

wherein G is C; Q is C; and R is selected from H, a substituted or unsubstituted alkyl, a fluorinated or partially fluorinated alkyl, a halogen, cyano, azido, hydroxyl, a substituted or unsubstituted sulfonyl;

Formula II

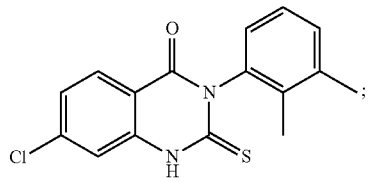

Formula III

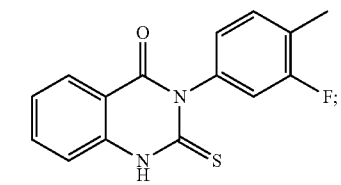

Formula IV

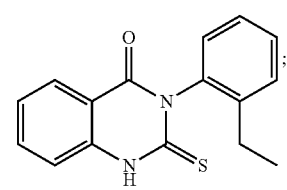

Formula V

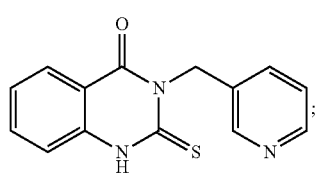

Formula VI

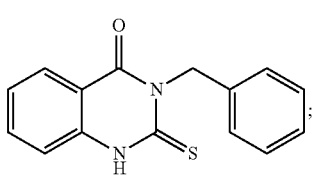

Formula VII

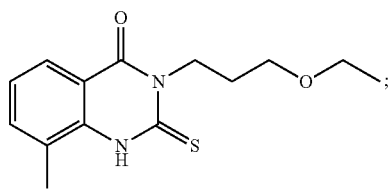

Formula VIII

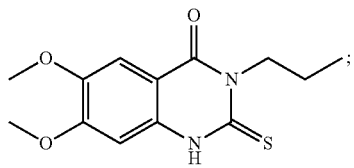

Formula X

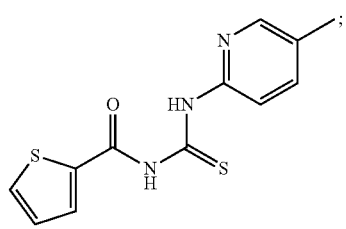

Formula XI

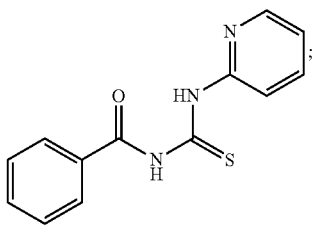

Formula XII

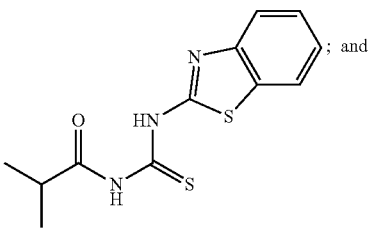

; and

Formula XIII

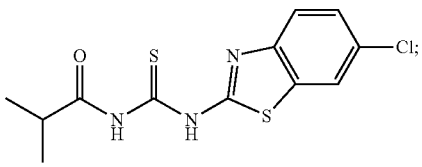

and a pharmaceutically acceptable buffer.

25. The pharmaceutical formulation of claim 24, further comprising an effective amount of a second antiproliferative agent compound.

26. The pharmaceutical formulation of claim 25, wherein the second antiproliferative agent is a platinum compound.

27. The pharmaceutical formulation of claim 26, wherein the platinum compound is cisplatin.

28. The pharmaceutical formulation of claim 26, wherein the platinum compound is carboplatin.

29. The pharmaceutical formulation of claim 24, wherein the compound is a compound having the Formula VII

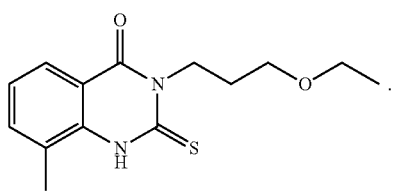 [SMILES: CCOCCCn1c(=S)[nH]c2c(C)cccc2c1=O]

30. A kit comprising a container comprising an effective amount of a compound for reducing cancer cell proliferation and/or promoting cancer cell death, having a formula selected from the group consisting of Formula I:

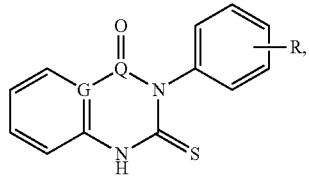

wherein G is C; Q is C; and R is selected from H, a substituted or unsubstituted alkyl, a fluorinated or partially fluorinated alkyl, a halogen, cyano, azido, hydroxyl, a substituted or unsubstituted sulfonyl;

Formula II

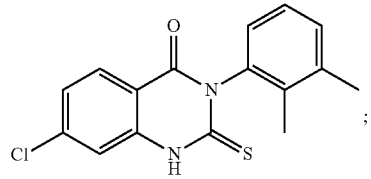

Formula III

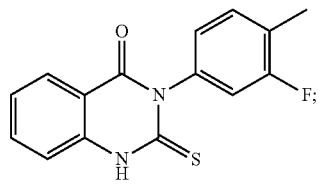

Formula IV

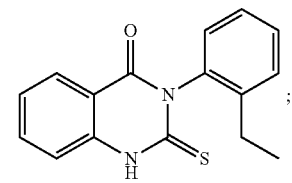

Formula V

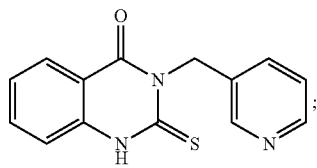

Formula VI

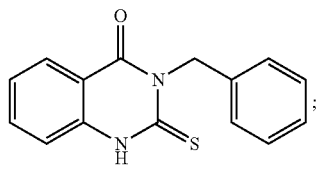

Formula VII

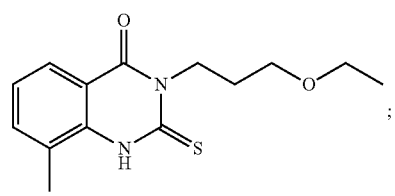

Formula VIII

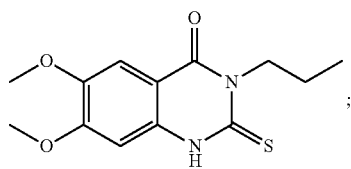

Formula X

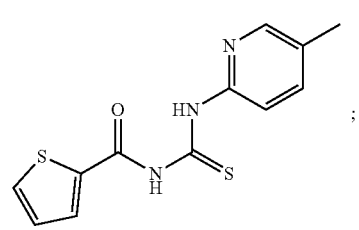

Formula XI

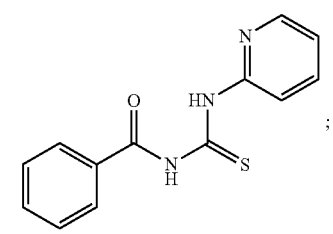

Formula XII

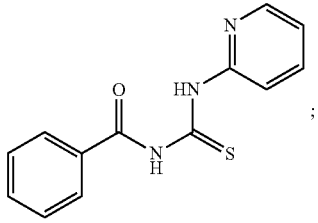

and

Formula XIII

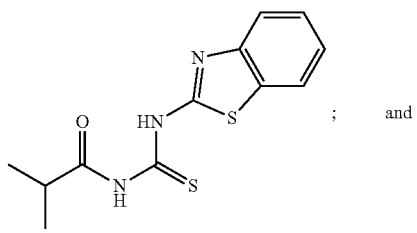

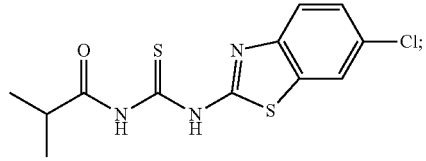

and a pharmaceutically acceptable buffer.

31. The kit of claim 30, further comprising an effective amount of a second antiproliferative agent compound.

32. The kit of claim 31, wherein the second antiproliferative agent is a platinum compound.

33. The kit of claim 32, wherein the platinum compound is cisplatin.

34. The kit of claim 32, wherein the platinum compound is carboplatin.

35. The kit of claim 30, wherein the compound is a compound having the Formula VII

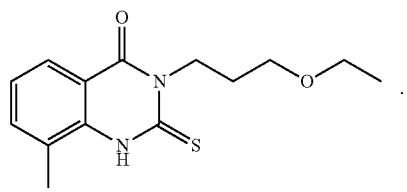 [SMILES: CCOCCCn1c(=S)[nH]c2c(C)cccc2c1=O]
* * * * *